(12) United States Patent
Gervais et al.

(10) Patent No.: US 7,311,893 B2
(45) Date of Patent: Dec. 25, 2007

(54) AMYLOID TARGETING IMAGING AGENTS AND USES THEREOF

(75) Inventors: Francine Gervais, Ile Bizard (CA); Xianqi Kong, Dollard-des-Ormeaux (CA); Robert Chalifour, Ile Bizard (CA); David Migneault, Laval (CA)

(73) Assignee: Neurochem (International) Limited, Lausanne (CH)

( * ) Notice: Subject to any disclaimer, the term of this patent is extended or adjusted under 35 U.S.C. 154(b) by 429 days.

(21) Appl. No.: 10/728,028

(22) Filed: Dec. 3, 2003

(65) Prior Publication Data

US 2005/0048000 A1  Mar. 3, 2005

Related U.S. Application Data

(63) Continuation-in-part of application No. 09/915,092, filed on Jul. 24, 2001, now abandoned.

(60) Provisional application No. 60/443,291, filed on Jan. 29, 2003, provisional application No. 60/220,808, filed on Jul. 25, 2000.

(51) Int. Cl.
  *A61K 51/00* (2006.01)
(52) U.S. Cl. ...................................................... 424/9.1
(58) Field of Classification Search ............... 424/1.11, 424/9.1, 9.3, 9.6; 514/554
See application file for complete search history.

(56) References Cited

U.S. PATENT DOCUMENTS

| | | | |
|---|---|---|---|
| 4,647,447 A | 3/1987 | Gries et al. | |
| 4,666,829 A * | 5/1987 | Glenner et al. ................ | 435/6 |
| 4,885,363 A | 12/1989 | Tweedle et al. | |
| 4,899,755 A | 2/1990 | Lauffer et al. | |
| 4,957,939 A | 9/1990 | Gries et al. | |
| 5,066,789 A | 11/1991 | Srinivasan et al. | |
| 5,088,499 A | 2/1992 | Unger | |
| 5,219,554 A | 6/1993 | Groman et al. | |
| 5,362,475 A | 11/1994 | Gries et al. | |
| 5,431,900 A | 7/1995 | Bergstein et al. | |
| 5,480,970 A | 1/1996 | Pollak et al. | |
| 5,558,854 A | 9/1996 | Quay | |
| 5,569,286 A | 10/1996 | Peckham et al. | |
| 5,573,751 A | 11/1996 | Quay | |
| 5,589,154 A | 12/1996 | Anderson | |
| 5,637,759 A | 6/1997 | Hearst et al. | |
| 5,643,562 A | 7/1997 | Kisilevsky et al. | |
| 5,659,041 A | 8/1997 | Pollak et al. | |
| 5,662,885 A | 9/1997 | Pollak et al. | |
| 5,674,470 A | 10/1997 | Tweedle et al. | |
| 5,676,925 A | 10/1997 | Klaveness et al. | |
| 5,725,373 A | 3/1998 | Yeh | |
| 5,795,562 A | 8/1998 | Klaveness et al. | |
| 5,820,850 A | 10/1998 | Hashimoto et al. | |
| 5,840,294 A | 11/1998 | Kisilevsky et al. | |
| 5,846,519 A | 12/1998 | Tweedle et al. | |
| 5,928,626 A | 7/1999 | Klaveness et al. | |
| 5,972,328 A | 10/1999 | Kisilevsky et al. | |
| 5,976,501 A | 11/1999 | Jablonski | |
| 6,033,645 A | 3/2000 | Unger et al. | |
| 6,053,930 A | 4/2000 | Ruppert | |
| 6,054,114 A | 4/2000 | Lansbury, Jr. et al. | |
| 6,071,495 A | 6/2000 | Unger et al. | |
| 6,083,484 A | 7/2000 | Lohrmann et al. | |
| 6,096,782 A * | 8/2000 | Audia et al. ................. | 514/506 |
| 6,123,920 A | 9/2000 | Gunther et al. | |
| 6,139,819 A | 10/2000 | Unger et al. | |
| 6,146,657 A | 11/2000 | Unger et al. | |
| 6,191,166 B1 * | 2/2001 | Audia et al. ................. | 514/534 |
| 6,197,040 B1 | 3/2001 | LeVaughn et al. | |
| 6,207,856 B1 * | 3/2001 | Veech ......................... | 560/178 |
| 6,211,235 B1 * | 4/2001 | Wu et al. .................... | 514/534 |
| 6,261,537 B1 | 7/2001 | Klaveness et al. | |
| 6,274,119 B1 | 8/2001 | Barrio et al. | |
| 6,670,399 B2 | 12/2003 | Green et al. | |
| 2002/0020087 A1 * | 2/2002 | Griffith ...................... | 40/124.4 |

FOREIGN PATENT DOCUMENTS

| | | | |
|---|---|---|---|
| WO | WO-00/64420 A2 | 11/2000 | |
| WO | WO0064420 | * 11/2000 | |
| WO | WO-01/39796 A2 | 6/2001 | |
| WO | WO-01/87534 A2 | 11/2001 | |
| WO | WO-02/24652 A1 | 3/2002 | |

OTHER PUBLICATIONS

Amedio, J.C. et al., "Preparation of N,N-Bis[2-N'N'-Bis[(Tert-Butoxycarbonyl) Methyl]-Amino]Ethyl-L-Aspartic Acid: An Intermediate In The Synthesis Of MRI Contrast Agents," *Synthetic Communications*, vol. 30(20):3755-3763 (2000).

Pollack, Scott J. et al., "Sulfonated dyes attenuate the toxic effects of β-amyloid in a structure-specific fashion," *Neuroscience Letters*, vol. 197:211-214 (1995).

Rudyk, Hélène et al., "Screening Congo Red and its analogues for their ability to prevent the formation of PrP-res in scrapie-infected cells," *Journal of General Virology*, vol. 81:1155-1164 (2000).

* cited by examiner

*Primary Examiner*—Michael G. Hartley
*Assistant Examiner*—Jagadishwar Samala
(74) *Attorney, Agent, or Firm*—Lahive & Cockfield, LLP; Danielle L. Herritt; Cynthia M. Soroos

(57) ABSTRACT

Amyloid-targeting imaging agents such as radiolabeled amyloid targeting molecules and amyloid targeting molecule-chelator conjugates for imaging, e.g., amyloid plaques in vivo, and/or for the treatment of amyloidosis disorders. The invention provides amyloid-targeting imaging agents that are useful for imaging sites of amyloid disease. Imaging agents of the invention are capable of binding specifically to amyloid plaques, as an aid in diagnosis and/or early treatment of amyloidosis disorders.

38 Claims, 2 Drawing Sheets

Figure 1

| Compound Name | MW | Structure | Bound (%) to fibrillar 1-40 | Bound to S 1-40 (Soluble) |
|---|---|---|---|---|
| sodium 1,6-hexanedisulfonate | 290.26 | $NaO_3SCH_2(CH_2)_4CH_2SO_3Na$ | ++ | — |
| 3-hydroxypropylsulfonic acid, disodium salt | 279.19 | $NaO_3SNHCH_2CH_2CH_2OSO_3Na$ | ++ | — |
| 4-(1-piperidinyl)-1-butanesulfonic acid | 221.31 | (piperidine-N-(CH₂)₄-SO₃H structure) | + | — |
| 1,4-piperazinebis(propanesulfonic acid) | 330.41 | $HO_3S(CH_2)_3$—N(piperazine)N—$(CH_2)_3SO_3H$ | ++ | — |
| 3-[1-(1,2,3,6-tetrahydropyridinyl)]-1-propanesulfonic acid | 205.27 | (tetrahydropyridine-N-(CH₂)₃-SO₃H structure) | ++ | — |

Figure 2

| Compound Name | MW | Structure | Bound (%) to fibrillar 1-40 | Bound to S 1-40 (Soluble) |
|---|---|---|---|---|
| Thiazole yellow G | 695.71 | 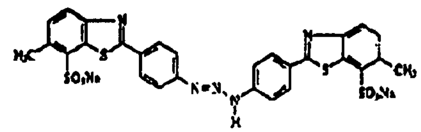 | +++ | − |
| alpha-N-(3-Sulfopropyl)-L-lysine | 268.33 | 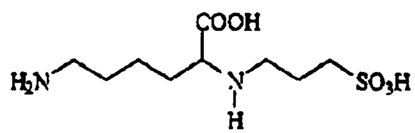 | ++ | − |
| 3-(6-Hydroxy-1hexyl)amino-1-propane sulfonic acid | 239.33 | 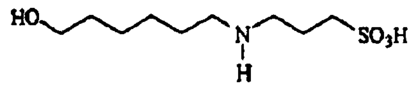 | ++ | − |
| 3-(1-Hydroxymethyl-1-cyclopentyl)amino-1-propanesulfonic acid | 237.31 | 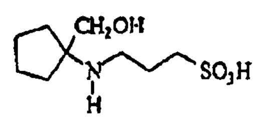 | + | − |
| Methyl 2-(2-carboxyethyl)-1,2,3,4-tetrahydroisoquinoline hydrochloride | 255.74 | 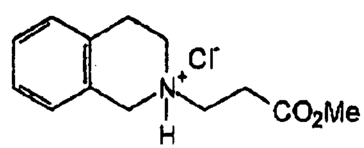 | +++ | − |

SEQUENCE LISTING

```
<160> NUMBER OF SEQ ID NOS: 28

<210> SEQ ID NO 1
<211> LENGTH: 6
<212> TYPE: PRT
<213> ORGANISM: Artificial Sequence
<220> FEATURE:
<223> OTHER INFORMATION: Synthetic Construct

<400> SEQUENCE: 1

Lys Ile Val Phe Phe Ala
 1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Lys Lys Leu Val Phe Phe Ala
 1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct

<400> SEQUENCE: 3

Lys Phe Val Phe Phe Ala
 1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Construct

<400> SEQUENCE: 4

Ala Phe Phe Val Leu Lys
 1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic Construct

<400> SEQUENCE: 5
```

Lys Leu Val Phe
1

<210> SEQ ID NO 6
<211> LENGTH: 6
<212> TYPE: PRT
<213> ORGANISM: Artificial Sequence
<220> FEATURE:
<223> OTHER INFORMATION: Synthetic Construct

<400> SEQUENCE: 6

Lys Ala Val Phe Phe Ala
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

Lys Leu Val Phe Phe
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct

<400> SEQUENCE: 8

Lys Val Val Phe Phe Ala
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Construct

<400> SEQUENCE: 9

Lys Ile Val Phe Phe Ala
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Construct

<400> SEQUENCE: 10

Lys Leu Val Phe Phe Ala
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Construct

<400> SEQUENCE: 11

```
Lys Phe Val Phe Phe Ala
 1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct

<400> SEQUENCE: 12

Ala Phe Phe Val Leu Lys
 1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic Construct

<400> SEQUENCE: 13

Lys Leu Val Phe
 1

<210> SEQ ID NO 14
<211> LENGTH: 6
<212> TYPE: PRT
<213> ORGANISM: Artificial Sequence
<220> FEATURE:
<223> OTHER INFORMATION: Synthetic Construct

<400> SEQUENCE: 14

Lys Ala Val Phe Phe Ala
 1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Construct

<400> SEQUENCE: 15

Lys Leu Val Phe Phe
 1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Construct

<400> SEQUENCE: 16

Lys Val Val Phe Phe Ala
 1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct

<400> SEQUENCE: 17

Lys Leu Val Phe Phe Ala Gln
```

-continued

```
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct

<400> SEQUENCE: 18

Lys Leu Val Phe Phe Ala Gln
 1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct

<400> SEQUENCE: 19

His His Gln Lys Leu Val Phe Phe Ala Gln
 1               5                  10

<210> SEQ ID NO 20
<211> LENGTH: 6
<212> TYPE: PRT
<213> ORGANISM: Artificial Sequence
<220> FEATURE:
<223> OTHER INFORMATION: Synthetic Construct

<400> SEQUENCE: 20

Lys Val Asp Asp Gln Asp
 1               5

<210> SEQ ID NO 21
<211> LENGTH: 4
<212> TYPE: PRT
<213> ORGANISM: Artificial Sequence
<220> FEATURE:
<223> OTHER INFORMATION: Synthetic Construct

<400> SEQUENCE: 21

His His Gln Lys
 1

<210> SEQ ID NO 22
<211> LENGTH: 5
<212> TYPE: PRT
<213> ORGANISM: Artificial Sequence
<220> FEATURE:
<223> OTHER INFORMATION: Synthetic Construct

<400> SEQUENCE: 22

Leu Val Phe Phe Ala
 1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Construct

<400> SEQUENCE: 23

Leu Val Phe Phe Ala
 1               5
```

```
<210> SEQ ID NO 24
<211> LENGTH: 5
<212> TYPE: PRT
<213> ORGANISM: Artificial Sequence
<220> FEATURE:
<223> OTHER INFORMATION: Synthetic Construct

<400> SEQUENCE: 24

Leu Val Phe Phe Ala
 1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Construct

<400> SEQUENCE: 25

Leu Val Phe Phe Ala
 1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct

<400> SEQUENCE: 26

Leu Val Phe Phe Ala
 1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Construct

<400> SEQUENCE: 27

Lys Leu Val Phe Phe Ala
 1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Construct

<400> SEQUENCE: 28

Lys Leu Val Phe Phe Ala
 1               5
```

AMYLOID TARGETING IMAGING AGENTS AND USES THEREOF

RELATED APPLICATIONS

This application claims the benefit of priority under 35 U.S.C. 119(e) to copending U.S. Provisional Application No. 60/443,291, filed Jan. 28, 2003. This application is also a continuation-in-part of U.S. patent application Ser. No. 09/915,092, filed Jul. 24, 2001 which claims priority to U.S. Provisional Application No. 60/220,808, filed Jul. 25, 2000, the entire contents of each of which are incorporated herein by reference.

BACKGROUND OF THE INVENTION

Amyloidosis refers to a pathological condition characterized by the presence of amyloid fibers. Amyloid is a generic term referring to a group of diverse but specific extracellular protein deposits which are seen in a number of different diseases. Though diverse in their occurrence, all amyloid deposits have common morphologic properties, stain with specific dyes such as Congo Red, and have a characteristic red-green birefringent appearance in polarized light after staining. They also share common ultrastructural features and common x-ray diffraction and infrared spectra.

Some amyloidotic diseases can be idiopathic but most of these diseases appear as a complication of a previously existing disorder. For example, primary amyloidosis can appear without any other pathology or can follow plasma cell dyscrasia or multiple myeloma. Secondary amyloidosis is usually seen associated with chronic infection such as tuberculosis, or chronic inflammation such as rheumatoid arthritis. A familial form of secondary amyloidosis is also seen in the Familial Mediterranean Fever (FMF). This familial type of amyloidosis, like the other types of familial amyloidosis, is genetically inherited and is found in specific group populations. Isolated forms of amyloidosis are those that tend to involve a single organ system. Different amyloids are also characterized by the type of protein present in the deposit. For example, neurodegenerative diseases such as scrapie, bovine spongiform encephalitis (BSE), Creutzfeldt-Jakob disease, and the like are characterized by the appearance and accumulation of a protease-resistant form of a prion protein (referred to as AScr or PrP-27) in the central nervous system. Similarly, Alzheimer's disease, another neurodegenerative disorder, is characterized by congophilic cerebral angiopathy, neuritic plaques and neurofibrillary tangles. In this case, the plaque and blood vessel amyloid is formed by the deposition of fibrillar Aβ amyloid protein. Other systemic diseases such as adult-onset diabetes, complications of long-term hemodialysis and sequelae of long-standing inflammation or plasma cell dyscrasias are characterized by the accumulation of amyloids systemically. Yet another amyloid-associated disease is cerebral amyloid angiopathy. In each of these cases, a different amyloidogenic protein is involved in amyloid deposition.

Each amyloidogenic protein can organize into β-sheets and form insoluble fibrils which get deposited extracellularly. Each amyloidogenic protein, although completely different in nature, has the same property of forming fibrils and binding to other elements such as proteoglycan (glycosaminoglycan, or "GAG"), amyloid P, and complement component. Moreover, each amyloidogenic protein has amino acid sequences which, although different, will show similarities such as regions (referred to as the GAG binding site) with the ability to bind to GAGs, as well as other regions which promote β-sheet formation.

In specific cases, once amyloidotic fibrils are deposited, they become toxic to the surrounding cells. Aβ fibrils organized as senile plaques have been shown to be associated with dead neuronal cells and microgliosis in patients with Alzheimer's disease. When tested in vitro, fibrillar Aβ peptide has been shown to be capable of triggering an activation process of the microglia (brain macrophages) in vitro which would explain the presence of microgliosis and brain inflammation found in the brain of patients with Alzheimer's disease.

In another type of amyloidosis seen in patients with Type II diabetes, the amyloidogenic protein IAPP has been shown to induce β-islet cell toxicity in vitro. Hence, appearance of IAPP fibrils in the pancreas of Type II diabetic patients could contribute to the loss of the β islet cells (Langerhans), and organ dysfunction.

Diagnostic medical imaging has become a critical element of modern health care. Ultrasound, radionuclide, x-ray, and magnetic resonance imaging techniques facilitate the diagnosis of disease. Each of these techniques expose a body to an energy source, e.g., sound, x-rays, radiation (either from an internal source, e.g., a radioactive pharmaceutical, or an external source), radio waves, etc., and monitor the characteristics of that energy as it interacts with the body. Diagnostic pharmaceuticals, frequently called contrast agents, may be simultaneously administered to a patient to augment the usefulness of the imaging technique itself by altering the energy or the way that energy interacts with tissues. Diagnostic medical imaging frequently uses targeted contrast agents that, in binding or localizing at sites selectively within the body, help to resolve an image of diagnostic interest. Targeted diagnostic imaging contrast agents generally consist of a targeting moiety labeled with a traceable moiety. Such traceable moieties include fluorescent tags; radio-opaque dyes (e.g., iodinated aromatics), radioactive elements such as $^3$H, $^{18}$F, $^{125}$I, $^{129}$I; or diagnostically useful chelated radioactive or paramagnetic metals such as Gd(III), Mn(II), Tc-99m, Re-186, Re-188, In-111, or Ga-67. The targeting moiety carries the label to the site of diagnostic interest where it is detected, e.g., by MRI, US, CT, or radionuclide imaging (including SPECT).

SUMMARY OF THE INVENTION

This invention relates to amyloid-targeting imaging agents such as labeled amyloid targeting molecules and amyloid targeting molecule-chelator conjugates for imaging amyloid plaques, e.g., in vivo. Certain of these amyloid-targeting imaging agents may alternatively be used for the treatment of amyloidosis disorders.

Imaging agents capable of binding specifically to amyloid fibrils and fibril-containing structures (e.g., lesions or plaques) as an aid in diagnosis and/or early treatment of amyloidosis disorders are highly desirable. An earlier diagnosis of an amyloidosis disorder will allow the practitioner to provide an appropriate therapy and thus may prevent undesirable effects of the disorder, such as the cytotoxicity caused by amyloid fibrils and/or plaques. Prior to the present invention, there has been no easy or reliable method of diagnosis for many amyloidosis-related disorders. For example, Alzheimer's disease is only definitively determined after death of the patient by autopsy. Other diseases often require biopsy which is invasive. Although certain proteins, peptides and antibodies that localize at desired regions of the human body have been utilized as targeting agents in diagnostic imaging, no known imaging agents are believed to exist for diagnosing amyloidosis related disorders such as Alzheimer's disease and systemic amyloidosis.

This invention provides amyloid-targeting imaging agents and methods for their use in diagnosis that are useful for imaging amyloid fibrils in vivo, e.g., amyloid plaques. Such amyloid-targeting imaging agents include those of Formula (I):

$$A_t\text{-}(A_{lnk})_z\text{-}A_{lab} \qquad (I)$$

where z is 0 or 1; $A_t$ is an amyloid targeting moiety; $A_{lnk}$ is a linker moiety; and $A_{lab}$ is a labeling moiety.

In one embodiment, the amyloid-targeting imaging agents desirably are capable of crossing the blood brain barrier, to allow imaging of, e.g., amyloid plaques in the brain. The amyloid-targeting moiety $A_t$ may be an amyloid-targeting compound such as a peptide of Formula II:

$$R'\text{—}(P)\text{—}R'' \qquad (II),$$

wherein
P is selected from the group consisting of peptides which interact with at least one region of an amyloid protein selected from the group consisting of β sheet region, macrophage adherence region, and GAG-binding site region, or Aβ (1-42), fragments or derivatives thereof; said peptide being comprised of natural or unnatural amino acids of either D or L stereochemical configuration;

R' is an N-terminal substituent selected from the group consisting of:
hydrogen;
lower alkyl groups (acyclic or cyclic having 1 to 8 carbon atoms) without or with substituent functional groups, e.g., carboxylate, sulfonate and phosphonate;
aromatic groups;
heterocyclic groups; and
acyl groups e.g., alkylcarbonyl, arylcarbonyl, sulfonyl and phosphonyl group; and R'' is a C-terminal substituent, e.g., hydroxy, alkoxy, aryloxy, unsubstituted or substituted amino groups.

In an embodiment, R' and R'' are identical or different, wherein an alkyl or aryl group of R' and R'' may be further substituted with an organic functionality such as a halide (F, Cl, Br, or I), hydroxyl, alkoxyl, aryloxyl, hydroxycarbonyl, alkoxylcarbonyl, aryloxycarbonyl, carbamyl, unsubstituted or substituted amino, sulfo or alkyloxysulfonyl, phosphono, or alkoxyphosphonyl group.

When the compound has an acid functional group, it can be in the form of a pharmaceutically acceptable salt or ester. When the compound has a basic functional group, it can be in the form of a pharmaceutically acceptable salt.

In another embodiment, the amyloid-targeting moiety $A_t$ is an amyloid-targeting compound having at least one anionic group covalently attached to a linking group. The amyloid-targeting moiety $A_t$ may be one of Formula III:

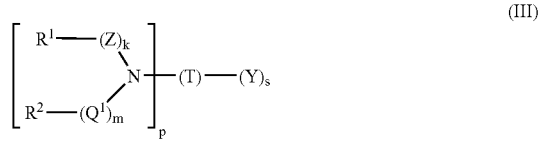

or a pharmaceutically acceptable salt or ester thereof. $R^1$ and $R^2$ are each independently a hydrogen atom or a substituted or unsubstituted aliphatic or aryl group. Z and $Q^1$ are each independently a carbonyl (C=O), thiocarbonyl (C=S), sulfonyl (SO$_2$), or sulfoxide (S=O) group. "k" and "m" are independently 0 or 1, provided when k is 1, $R^1$ is not a hydrogen atom, and when m is 1, $R^2$ is not a hydrogen atom. In an embodiment, at least one of k or m must equal 1. "p" and "s" are each independently positive integers selected such that the resulting compound is stable and useful as a diagnostic or therapeutic drug and the drug has an affinity for a target. T is a linking group and Y is a group of the formula -AX, wherein A is an anionic group at physiological pH, and X is a cationic group. Linking group T is, in some cases, advantageously of the formula $\text{-}(CD^1D^2)_n\text{-}$, wherein n is an integer from 1 to 25, C is carbon and $D^1$ and $D^2$ are independently a hydrogen or halogen atom; aliphatic, aromatic or heterocyclic group; alkylamino or arylamino group; or alkyloxy or aryloxy group. In another embodiment, the amyloid-targeting moiety $A_t$ prevents or inhibits amyloid aggregation.

In another embodiment, $R^1$ is an alkyl, alkenyl, or aryl group; k is one; Z is a carbonyl group; $R^2$ is a hydrogen atom or an alkyl group; m is zero; p and s are 1; T is an alkylene group; and $Y^1$ is $SO_3X^2$, where $X^2$ is H or another physiologically acceptable cation, e.g., cations of alkali metals including Li, Na, and K.

In another embodiment, $R^1$ and $R^2$ are alkyl, alkenyl, or aryl, or $R^1$ and $R^2$, taken together, form an alkylene group; k and m are each one; Z and $Q^1$ are carbonyl groups; p and s are 1; T is an alkylene group; and $Y^1$ is $SO_3X^2$, where $X^2$ is H or another physiologically acceptable cation.

In a further embodiment, $R^1$ is an alkyl, alkenyl, or aryl; k and m are zero; $R^2$ is hydrogen or an alkyl group, p and s are each one; T is an alkylene group; and $Y^1$ is $SO_3X^2$, wherein $X^2$ is H$^+$ or another physiologically acceptable cation.

In another embodiment, $R^1$ and $R^2$ are alkyl, alkenyl, or aryl, or $R^1$ and $R^2$, taken together, form an alkylene group; k and m are zero; p and s are each one; T is an alkylene group; and $Y^1$ is $SO_3X^2$, where $X^2$ is H$^+$ or another physiologically acceptable cation.

$A_t$ may also be of Formula IIIa:

where $R^1$ is an alkyl, alkenyl, hydroxyalkyl, or a single-ring aromatic group; $R^2$ is a alkyl, alkenyl, hydroxyalkyl, a single-ring aromatic group, or a hydrogen atom, or $R^1$ and $R^2$, taken together with the nitrogen to which they are attached, form a heterocyclic group which is a fused ring structure; T is an alkylene group; Y is $SO_3X$, and X is a cationic group. In another embodiment, $A_t$ may be of Formula IIIa where $R^1$ is a $C_5$-$C_{18}$ alkyl, hydroxyalkyl or single-ring aromatic group; $R^2$ is a hydrogen atom or an alkyl group; T is an alkylene group; Y is $SO_3X$, and X is a cationic group. In yet another embodiment, $A_t$ may be of Formula IIIa where $R^1$ and $R^2$ are alkyl, alkenyl, or single-ring aromatic groups, or $R^1$ and $R^2$, taken together with the nitrogen to which they are attached, form a heterocyclic group which is a fused ring structure; T is an alkylene group; Y is $SO_3X$, and X is a cationic group.

$A_t$ may also be of Formula IIIb:

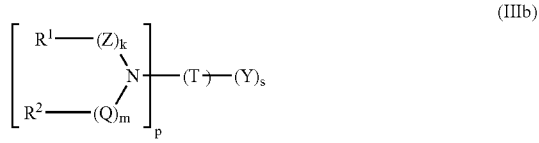

where $R^1$ is an alkyl, an alkenyl, or an aromatic group; $R^2$ is a hydrogen atom, an alkyl group, or an aromatic group, or $R^1$ and $R^2$, taken together, form a heterocyclic group which is a fused ring structure; Z and Q are each independently a carbonyl (C=O), thiocarbonyl (C=S), sulfonyl ($SO_2$), or sulfoxide (S=O) group; k is 1 and m is 0 or 1; p and s are each 1; T is an alkylene group; Y is $SO_3X$, and X is a cationic group.

The linker moiety $A_{lnk}$ allows for attachment of an labeling moiety $A_{lab}$ to amyloid-targeting moiety $A_t$. Examples of $A_{lnk}$ include amino, alkylamino, arylamino, oxo, alkoxy, oxoalkyl, aryloxy, oxoaryl, thio, alkylthio, thioalkyl, arylthio, thioaryl, carbonyl, alkylcarbonyl, carbonylalkyl, arylcarbonyl, carbonylaryl, carboxyl, alkylcarboxyl, arylcarboxyl, alkyl, alkylenyl, alkenyl, alkynyl, aryl groups. In certain embodiments, $A_{lnk}$ is optional. Preferred linker moieties include, among others, glucose and Phe.

Once at the target site in vivo, e.g., amyloid plaques, labeling moiety $A_{lab}$ allows an amyloid-targeting imaging agent of the invention to be visualized by CT, MRI, ultrasound, radioisotopic or fluorescence detection. In one embodiment, labeling moiety $A_{lab}$ may be a metal chelate, e.g., a chelate of a metal with a ligand of Formula VII. In an advantageous embodiment, $A_{lab}$ includes a radionuclide. In cases where the amyloid-targeting imaging agent includes a labeling moiety $A_{lab}$ (e.g., including a radionuclide) attached directly to amyloid-targeting moiety $A_t$, linker moiety $A_{lnk}$ may be optional.

Labeling moieties $A_{lab}$ may advantageously include diagnostically or therapeutically useful radionuclides such as $^3H$, $^{129}I$, $^{125}I$, $^{131}I$, or $^{18}Fe$ for use as radiopharmaceuticals. In one embodiment the labeling moiety $A_{lab}$ includes, without limitation, Tc or Re. The labeling moiety $A_{lab}$ may also be a combination of radionuclide(s) and a metal chelator (such as described below).

In a particular embodiment of the invention, labeling moiety $A_{lab}$ may be a metal chelate comprising a ligand of the formula:

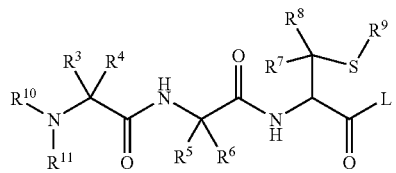

where $R^{10}$ is a linear or branched, saturated or unsaturated $C_{1-4}$ alkylene group interrupted by one or two heteroatoms, e.g., N, O, or S. $R^{10}$ may also be optionally substituted by one or more of halogen, hydroxyl, amino, carboxyl, $C_{1-4}$ alkyl, aryl, and C(O)R groups. $R^{11}$ is H or $R^{10}$; $R^{10}$ and $R^{11}$ may, taken together, form a 5- to 8-membered saturated or unsaturated heterocyclic ring optionally substituted one or more of halogen, hydroxyl, amino, carboxyl, oxo, $C_{1-4}$ alkyl, aryl, or C(O)R groups. $R^3$, $R^4$, $R^5$ and $R^6$ may independently be H, carboxyl, $C_{1-4}$ alkyl (optionally substituted with, e.g., hydroxyl, amino, sulfhydryl, halogen, carboxyl, $C_{1-4}$ alkoxycarbonyl, or aminocarbonyl groups), an alpha carbon side chain of a D- or L-amino acid other than proline, and C(O)R. $R^7$ and $R^8$ may independently be H, carboxyl, amino, $C_{1-4}$ alkyl, $C_{1-4}$ alkyl (optionally substituted with, e.g., hydroxyl, carboxyl, amino, or C(O)R); $R^9$ may be H or a sulfur protecting group; and L may be hydroxyl, alkoxy, an amino acid residue, or a linking group. Other chelating ligands are contemplated by the instant invention as explained further herein.

Methods of the invention also include administration to a subject of an amyloid-targeting imaging agent where amyloid-targeting moiety $A_t$ has at least one anionic group covalently attached to a carrier molecule and is capable of inhibiting an interaction between an amyloidogenic protein and a glycoprotein or proteoglycan constituent of a basement membrane to inhibit amyloid deposition. In this embodiment, the amyloid-targeting moiety is:

wherein $Y^-$ is an anionic group at physiological pH; $Q^b$ is a carrier molecule; $X^+$ is a cationic group; and $n^2$ is an integer selected such that the biodistribution of the targeting moiety for the intended target site is not prevented while maintaining activity of the targeting moiety.

In another embodiment, the anionic group Y is a sulfonate group. Accordingly, in this embodiment the targeting moiety is:

In yet another embodiment, the anionic group Y is a sulfate group. Accordingly, in this embodiment the targeting moiety is:

The anionic group Y may also be a tetrazole group. $Q^b$ may be carbohydrates, polymers, peptides, peptide derivatives, aliphatic groups, alicyclic groups, heterocyclic groups, aromatic groups or combinations thereof.

The methods of the invention include administering to a subject an amyloid-targeting imaging agent having an amyloid-targeting moiety $A_t$, which inhibits, reduces or disrupts amyloid deposits; and pharmaceutical compositions comprising an amyloid-targeting imaging agent in an amount effective to modulate amyloid aggregation, and a pharmaceutically acceptable vehicle.

In another aspect of the invention, diagnostic kits are provided which include amyloid targeting imaging agents as described herein; a reducing agent; a buffering agent; a transchelating agent, and instructions for use of the kit. The kit generally provides all the components required to prepare, e.g., a detectable labeled conjugate for diagnostic use, possibly with the exception of the detectable label which is desirably generated at the clinical site. The components of the kit can be provided in powder form that is readily prepared into an injectable solution on reconstitution with an aqueous solvent. This solution can then be admixed with an appropriate amount of detectable label, e.g., radionuclide metal appropriate for the imaging technique to be employed, and immediately used to image a target site.

DETAILED DESCRIPTION OF THE INVENTION

FIG. 1 and FIG. 2 show binding data for amyloid-targeting moieties of the invention.

DETAILED DESCRIPTION OF THE INVENTION

The invention will be more fully illustrated by reference to the definitions set forth below.

"Amyloid-targeting imaging agents" includes radiolabeled amyloid targeting molecules, amyloid targeting molecule-chelator conjugates, and amyloid targeting molecule derivative-chelator conjugates, for imaging amyloid plaques, e.g., in vivo, and/or for the treatment of amyloidosis disorders, such as described herein. Such imaging agents preferably bind to insoluble amyloid in preference to soluble amyloid.

"Amyloid-targeting molecules" includes labeled molecules such as described herein which comprise an amyloid targeting moiety and associate or bind with amyloid fibrils or structures, lesions, or the like which contain amyloid fibrils, e.g., amyloid plaques. Preferably such targeting molecules bind preferentially to insoluble fibrillary amyloid and only minimally bind to soluble monomeric or oligomeric amyloid. The insoluble fibrillary amyloid is typically the type of amyloid commonly associated with amyloid-related diseases.

"Amyloid targeting molecule-chelator conjugates" include compositions such as described herein, having a labeling moiety comprising a metal chelator.

The term "alkyl" includes saturated aliphatic groups (methyl, ethyl, propyl, butyl, pentyl, hexyl, heptyl, octyl, nonyl, decyl, etc.), including straight-chain alkyl groups, branched-chain alkyl groups (iso-propyl, iso-butyl, sec-butyl, tert-butyl, neopentyl, etc.), cycloalkyl (alicyclic) groups (cyclopropyl, cyclobutyl, cyclopentyl, cyclohexyl, etc.), alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably has 20 or fewer carbon atoms in the backbone, even more preferably $C_1$-$C_8$. Likewise, cycloalkyls may have from 4-10, more preferably 5, 6 or 7, carbon atoms in their ring structure.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, a halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl(benzyl)).

The term "aryl" herein includes 5- and 6-membered single-ring aromatic groups that may include from zero to four heteroatoms, for example, benzene, pyrrole, furan, thiophene, imidazole, oxazole, thiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, a halogen, hydroxyl, aryloxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" include unsaturated aliphatic groups analogous in length and possible substitution to the alkyls described above, but that contain at least one double or triple bond respectively.

Unless the number of carbons is otherwise specified, "lower alkyl" means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

"Carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

The terms "heterocyclyl" or "heterocyclic group" include 3- to 10-membered ring structures, more preferably 4- to 7-membered rings, which ring structures include one to four heteroatoms. Heterocyclyl groups include pyrrolidine, oxolane, thiolane, piperidine, piperazine, morpholine, lactones, lactams such as azetidinones and pyrrolidinones, sultams, sultones, and the like. The nitrogen and sulfur heteroatoms may optionally be oxidized. The heterocyclic ring may be attached to its pendant group at any heteroatom or carbon atom that results in a stable structure. The heterocyclic ring may be substituted on carbon or on a nitrogen atom if the resulting compound is stable. The heterocyclic ring can be substituted at one or more positions with such substituents as described above, as for example, a halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, or an aromatic or heteroaromatic moiety. A nitrogen in a heterocycle may optionally be quaternized.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl groups. Also included are fused ring and spiro compounds containing, for example, the above heterocycles.

"Polycyclyl" or "polycyclic group" includes two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, a halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, or an aromatic or heteroaromatic moiety.

"Heteroatom" includes atoms of any element other than carbon or hydrogen. Preferred heteroatoms are nitrogen, oxygen, sulfur and phosphorus.

"Aryl aldehyde" includes compounds represented by the formula Ar—C(O)H, in which Ar is an aryl moiety (as described above) and —C(O)H is a formyl or aldehydo group.

"Inhibition" of amyloid deposition includes preventing or stopping of amyloid formation, e.g., fibrillogenesis, inhibiting or slowing down of further amyloid deposition in a subject with amyloidosis, e.g., already having amyloid deposits, and reducing or reversing amyloid fibrillogenesis or deposits in a subject with ongoing amyloidosis. Inhibition of amyloid deposition is determined relative to an untreated subject, or relative to the treated subject prior to treatment, or, e.g., determined by clinically measurable improvement in pancreatic function in a diabetic patient or an increase in the memory function of an Alzheimer's patient. Alternatively, the targeting moiety may be assayed either by itself or as a conjugate with a labeling moiety according to the invention in an in vitro assay which predicts in vivo function.

"Sulfur protecting group" includes chemical groups bonded to a sulfur atom and inhibits oxidation of sulfur and includes groups that are cleaved upon chelation of the metal. Suitable sulfur protecting groups include without limitation alkyl, aryl, acyl, alkanoyl, aryloyl, mercaptoacyl, and organothio groups. Common protecting group strategies are described in "Protecting Groups in Organic Synthesis, Third Ed." By P. Wuts and T. Greene, © 1999 John Wiley & Sons, Inc.

"Thiol" includes sulfhydryl groups, e.g., that may be substituted with an alkyl group to form thioethers.

"Metal chelator" includes molecules that form stable complexes with traceable metal atoms under physiological conditions such that the metal remains bound in vivo. For diagnostic imaging purposes, a chelator is a compound which has a reactive functional group for labeling by a radionuclide and, on binding to a radionuclide metal, forms a complex that is stable under physiological conditions. The term "chelate" refers to a polydentate ligand-metal ion complex. Typically, chelates are 1:1 stoicheometry in metal: chelator. Preferably, a chelate does not substantially dissociate in vivo.

"Carbohydrate" includes substituted and unsubstituted mono-, oligo-, and polysaccharides. Monosaccharides are simple sugars usually of the formula $C_6H_{12}O_6$ that can be linked to form oligosaccharides or polysaccharides. Monosaccharides include enantiomers and both the D and L stereoisomers of monosaccharides. Carbohydrates can have multiple anionic groups attached to each monosaccharide moiety. For example, in sucrose octasulfate, four sulfate groups are attached to each of the two monosaccharide moieties.

"Polymer" includes molecules formed by the chemical union of two or more combining subunits called monomers. Monomers are molecules or compounds which usually contain carbon and are of relatively low molecular weight and simple structure. A monomer can be converted to a polymer by combination with itself or other similar molecules or compounds. A polymer may be composed of a single identical repeating subunit or multiple different repeating subunits (copolymers).

"Retro isomer" refers to a reversal of the direction of the peptide backbone.

"Inverso isomer" refers to an inversion of the amino acid chirality used to make the peptide.

"Retro-inverso isomer" refers to a reversal of both the peptide backbone direction and the amino acid chirality.

"Amino acid" includes organic compounds containing both a basic amino group and an acidic carboxyl group. Included within this term are natural amino acids (e.g., L-amino acids), modified and unusual amino acids (e.g., D-amino acids and β-amino acids), as well as amino acids which are known to occur biologically in free or combined form but usually do not occur in proteins. Natural protein occurring amino acids include alanine, arginine, asparagine, aspartic acid, cysteine, glutamic acid, glutamine, glycine, histidine, isoleucine, leucine, lysine, methionine, phenylalanine, serine, threonine, tyrosine, tryptophan, proline, and valine. Natural non-protein amino acids include arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5,-triiodothyronine, and 3,3',5,5'-tetraiodothyronine. Modified or unusual amino acids include D-amino acids, hydroxylysine, 4-hydroxyproline, N-Cbz-protected amino acids, 2,4-diaminobutyric acid, homoarginine, norleucine, N-methylaminobutyric acid, naphthylalanine, phenylglycine, α-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

"Peptide" includes linear compounds that consist of two or more amino acids that are linked by means of a peptide bond. Peptides may have a molecular weight of less than 10,000 Daltons, preferable less than 5,000 Daltons, and more preferably less than 2,500 Daltons. The term "peptide" also includes compounds containing both peptide and non-peptide components, such as pseudopeptide or peptidomimetic residues or other non-amino acid components. Such compounds containing both peptide and non-peptide components may also be referred to as a "peptide analog".

"Pseudopeptide" or "peptidomimetic" is a compound which mimics the structure of an amino acid residue or a peptide, for example, by using linking groups other than amide linkages between the peptide mimetic and an amino acid residue (pseudopeptide bonds) and/or by using non-amino acid substituents and/or a modified amino acid residue. A "pseudopeptide residue" means that portion of a pseudopeptide or peptidomimetic that is present in a peptide.

"Pseudopeptide bonds" includes peptide bond isosteres, which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation.

"Pharmaceutically acceptable" includes those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salts" includes derivatives of compounds modified by making acid or base salts thereof. Examples of pharmaceutically acceptable salts include mineral or organic acid salts of basic residues such as amines; and alkali or organic salts of acidic residues such as carboxylic acids. Pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acid; and the salts prepared from organic acids such as acetic, propionic, succinic, glycolic, stearic, lactic, malic, tartaric, citric, ascorbic, palmoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic acid. Pharmaceutically acceptable salts can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two.

"Lipids" include synthetic or naturally-occurring compounds which are generally amphipathic and biocompatible. The lipids typically comprise a hydrophilic component and a hydrophobic component. Exemplary lipids include fatty acids, neutral fats, phosphatides, glycolipids, aliphatic alcohols, waxes, terpenes, steroids and surfactants. "Lipid composition" refers to a composition which comprises a lipid compound, typically in an aqueous medium. Exemplary lipid compositions include suspensions, emulsions and vesicle compositions.

"Vesicle" refers to a spherical entity which is generally characterized by the presence of one or more walls or membranes which form one or more internal voids. Vesicles may be formulated, for example, from lipids, including the various lipids described herein, proteinaceous materials, or polymeric materials, including natural, synthetic and semi-synthetic polymers. Preferred vesicles are those which comprise walls or membranes formulated from lipids. In these preferred vesicles, the lipids may be in the form of a monolayer or bilayer, and the mono- or bilayer lipids may be used to form one or more mono- or bilayers. In the case of more than one mono- or bilayer, the mono- or bilayers may be concentric. Lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). Similarly, the vesicles prepared from proteins or polymers may comprise one or more concentric walls or membranes. The walls or membranes of vesicles prepared from proteins or polymers may be substantially solid (uniform), or they may be porous or semi-porous. The vesicles described herein include such entities commonly referred to as, for example, liposomes, micelles, bubbles, microbubbles, microspheres, lipid-, polymer- and/or protein-coated bubbles, microbubbles and/or microspheres, microballoons, aerogels, clathrate bound vesicles, and the like. The internal void of the vesicles may be filled with a liquid (e.g., an aqueous liquid), a gas, a gaseous precursor, and/or a solid or solute material, including, e.g., a targeting ligand and/or a bioactive agent, as desired.

"Liposome" refers to a generally spherical cluster or aggregate of amphipathic compounds, including lipid compounds, typically in the form of one or more concentric layers, for example, bilayers. They may also be referred to herein as lipid vesicles. The liposomes may be formulated, for example, from ionic lipids and/or non-ionic lipids. Liposomes which are formulated from non-ionic lipids may also be referred to as "niosomes."

"Micelle" refers to colloidal entities formulated from lipids. In certain preferred embodiments, the micelles comprise a monolayer or hexagonal $H_2$ phase configuration. In other preferred embodiments, the micelles may comprise a bilayer configuration.

"Clathrate" refers to a solid, semi-porous or porous particle which may be associated with vesicles. In preferred form, the clathrates may form a cage-like structure containing cavities which comprise the vesicles. One or more vesicles may be bound to the clathrate. A stabilizing material may, if desired, be associated with the clathrate to promote the association of the vesicle with the clathrate. Suitable materials from which clathrates may be formulated include porous apatites, such as calcium hydroxyapatite, and precipitates of polymers and metal ions, such as alginic acid precipitated with calcium salts.

"Vesicle composition" refers to a composition, typically in an aqueous medium, which comprises vesicles.

"Emulsion" refers to a mixture of two or more generally immiscible liquids, and is generally in the form of a colloid which, upon drying, forms a porous solid matrix. The solid matrix is porous, i.e., the matrix forms a lattice with microvoids or microcavities, as a result, for example, of a spray drying blowing agent used in the drying process. The mixture may comprise lipids, which may be homogeneously or heterogeneously dispersed throughout the emulsion. Alternatively, the lipids may be aggregated in the form of, for example, clusters or layers, including mono- or bilayers.

"Suspension" or "dispersion" refers to a mixture, preferably finely divided, of two or more phases (solid, liquid or gas), such as liquid in liquid, solid in liquid, gas in liquid, and the like, which can preferably remain stable for extended periods of time.

"Imaging agent", or "contrast agent", or simply "agent", which terms may be used interchangeably, refers to any agent which may be used in connection with methods for imaging an internal region of a patient and/or diagnosing the presence or absence of a disease in a patient by the application and/or detection of an energy source. Exemplary imaging agents include contrast agents for use in connection with ultrasound, magnetic resonance imaging, radionuclide imaging, or x-ray (including computed tomography) imaging of a patient, and the compositions described herein.

"Polymer", as used herein, refers to molecules formed from the chemical union of two or more repeating units. Accordingly, included within the term "polymer" may be, for example, dimers, trimers and oligomers. The polymer may be synthetic, naturally-occurring or semisynthetic.

"Covalent association" refers to an intermolecular association or bond which involves the sharing of electrons in the bonding orbitals of two atoms.

"Non-covalent association" refers to intermolecular interaction among two or more separate molecules which does not involve a covalent bond. Intermolecular interaction is dependent upon a variety of factors, including, for example, the polarity of the involved molecules, the charge (positive or negative), if any, of the involved molecules, and the like. Non-covalent associations may be ionic or electrostatic interaction, dipole-dipole interaction and van der Waals forces, pi-stacking, Lewis acid/base coordination, or combinations thereof.

"Biocompatible" refers to materials which are generally not injurious to biological functions and which will not result in any degree of unacceptable toxicity, including allergenic responses and disease states.

A "precursor" to a targeting moiety refers to any material or substance which may be converted to a targeting moiety. Such conversion may involve, for example, anchoring a precursor to a targeting moiety. Exemplary targeting precursor moieties include maleimide groups, disulfide groups, such as ortho-pyridyl disulfide, vinylsulfone groups, azide groups, and α-iodo acetyl groups.

It will be noted that the structures of some of the compounds of this invention include asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, alkenes can include either the E- or Z-geometry, where appropriate.

In general, the abbreviations used herein for designating the amino acids and the protective groups are based on recommendations of the IUPAC-IUB Commission on Biochemical Nomenclature (*Biochemistry*, 11 1726-1732 (1972)).

The invention includes imaging compounds which will target amyloid in vivo. Such amyloid-targeting imaging agents include those of the formula:

(I)

wherein $A_t$ is an amyloid targeting moiety; $A_{lnk}$ is a linker moiety; and $A_{lab}$ is a labeling moiety.

The amyloid-targeting moiety $A_t$ associates or binds with amyloid fibrils or structures, lesions, or the like which contain amyloid fibrils, e.g., amyloid plaques. $A_t$ is a moiety or compound which targets, associates or binds with insoluble amyloid or amyloid plaques in preference to soluble amyloid or soluble oligomeric amyloid. $A_t$ is linked to the linker moiety, when present, or to the labeling moiety, e.g., covalently. The amyloid-targeting imaging agents desirably are capable of crossing the blood-brain barrier, to allow imaging, e.g., of amyloid plaques in the brain.

Some examples of preferred amyloid-targeting moieties according to the invention which bind insoluble amyloid or amyloid plaques in preference to soluble amyloid (see data in FIGS. 1 and 2) are 1,6-hexanedisulfonate (including the sodium salt thereof), 3-hydroxypropylsulfamic acid (including the disodium salt thereof), 4-(1-piperidinyl)-1-butanesulfonic acid, 1,4-piperazinebis(propanesulfonic acid), 3-[1-(1,2,3,6-tetrahydropyridinyl)]-1-propanesulfonic acid, Thiazole yellow G, alpha-N-(3-sulfopropyl)-L-lysine, 3-(6-hydroxy-1-hexyl)amino-1-propane sulfonic acid, 3-(1-hydroxymethyl-1-cyclopentyl)amino-1-propane sulfonic acid, and methyl 2-(2-carboxyethyl)-1,2,3,4-tetrahydroisoquinoline hydrochloride).

Further examples of preferred amyloid-targeting moieties according to the invention include 2-(3-sulfopropyl)-7-amino-1,2,3,4-tetrahydroisoquinoline, 3-[2-(5-amino-1,2,3,4-tetrahydroisoquinolinyl)]-1-propane sulfonic acid, 2-(3-sulfopropyl)-6-amino-1,2,3,4-tetrahydro-9H-pyrrido[3,4b]indole, 2-(4-sulfobutyl)-6-amino-1,2,3,4-tetrahydro-9H-pyrido[3,4b]indole, and pharmaceutically acceptable salts thereof, including the hydrochloride and sodium salts.

The amyloid-targeting moiety $A_t$ may be an amyloid-targeting compound such as a peptide of Formula II, a L or D isomer thereof, a retro or a retro-inverso isomer thereof, or a peptidomimetic thereof:

(II), wherein
P is selected from the group consisting of peptides which interact with at least one region of an amyloid protein selected from the group consisting of β sheet region, macrophage adherence region, and GAG-binding site region, or Aβ (1-42), fragments or derivatives thereof; said peptide being comprised of natural or unnatural amino acids of either D or L stereochemical configuration;

R' is an N-terminal substituent selected from the group consisting of:
hydrogen;
lower alkyl groups (acyclic or cyclic having 1 to 8 carbon atoms) without or with substituent functional groups, e.g., carboxylate, sulfonate and phosphonate;
aromatic groups;
heterocyclic groups; and
acyl groups e.g., alkylcarbonyl, arylcarbonyl, sulfonyl and phosphonyl group; and R" is a C-terminal substituent e.g., hydroxy, alkoxy, aryloxy, unsubstituted or substituted amino groups.

In an embodiment, R' and R" are identical or different, wherein an alkyl or aryl group of R' and R" may be further substituted with an organic functionality such as a halide (F, Cl, Br, or I), hydroxyl, alkoxyl, aryloxyl, hydroxycarbonyl, alkoxylcarbonyl, aryloxycarbonyl, carbamyl, unsubstituted or substituted amino, sulfo or alkyloxysulfonyl, phosphono, or alkoxyphosphonyl group.

When the compound has an acid functional group, it can be in the form of a pharmaceutically acceptable salt or ester. When the compound has a basic functional group, it can be in the form of a pharmaceutically acceptable salt.

In one preferred embodiment, peptides are full-length amyloid peptide and truncated versions thereof derived from said full-length peptide by removal of terminal amino acids. The amino acids may be of either D or L stereochemical configuration.

In one embodiment, the preferred compounds are selected from the full-length peptide, Aβ (1-42), and its lower homologues consisting of Aβ (1-40), Aβ (13-16), Aβ (1-35), and Aβ (1-28), each of which are preferably comprised of amino acids of D stereochemistry.

In another embodiment, the preferred compounds are selected from a group of short peptides consisting of Aβ (1-7), Aβ (10-16), Aβ (16-21), Aβ (36-42), each of which are preferably comprised of amino acids of D stereochemistry. The peptides can be shortened further by removing one or more residues from either end or both ends.

In another embodiment, preferred compounds are peptides derived from the above-said peptides by substitution of one or more residues in the naturally occurring sequence, preferably with amino acids of D stereochemistry.

In yet another embodiment, preferred compounds are peptidomimetics of the above-said peptides.

The following are exemplary compounds:

1  Aβ (1-42)
2  Aβ (1-40)
3  Aβ (1-35)
4  Aβ (1-28)
5  Aβ (1-7)
6  Aβ (10-16)
7  Aβ (16-21)
8  Aβ (36-42)
9  Aβ (13-16)
10 Lys-Ile-Val-Phe-Phe-Ala              (SEQ ID NO:1)
11 Lys-Lys-Leu-Val-Phe-Phe-Ala          (SEQ ID NO:2)
12 Lys-Phe-Val-Phe-Phe-Ala              (SEQ ID NO:3)
13 Ala-Phe-Phe-Val-Leu-Lys              (SEQ ID NO:4)
14 Lys-Leu-Val-Phe                      (SEQ ID NO:5)
15 Lys-Ala-Val-Phe-Phe-Ala              (SEQ ID NO:6)
16 Lys-Leu-Val-Phe-Phe                  (SEQ ID NO:7)
17 Lys-Val-Val-Phe-Phe-Ala              (SEQ ID NO:8)
18 Lys-Ile-Val-Phe-Phe-Ala-$NH_2$       (SEQ ID NO:9)
19 Lys-Leu-Val-Phe-Phe-Ala-$NH_2$       (SEQ ID NO:10)
20 Lys-Phe-Val-Phe-Phe-Ala-$NH_2$       (SEQ ID NO:11)
21 Ala-Phe-Phe-Val-Leu-Lys-$NH_2$       (SEQ ID NO:12)
22 Lys-Leu-Val-Phe-$NH_2$               (SEQ ID NO:13)
23 Lys-Ala-Val-Phe-Phe-Ala-$NH_2$       (SEQ ID NO:14)
24 Lys-Leu-Val-Phe-Phe-$NH_2$           (SEQ ID NO:15)
25 Lys-Val-Val-Phe-Phe-Ala-$NH_2$       (SEQ ID NO:16)
26 Lys-Leu-Val-Phe-Phe-Ala-Gln          (SEQ ID NO:17)
27 Lys-Leu-Val-Phe-Phe-Ala-Gln-$NH_2$   (SEQ ID NO:18)
28 His-His-Gln-Lys-Leu-Val-Phe-Phe-Ala-Gln  (SEQ ID NO:19)
29 Asp-Asp-Asp
30 Lys-Val-Asp-Asp-Gln-Asp              (SEQ ID NO:20)
31 His-His-Gln-Lys                      (SEQ ID NO:21)
32 Phe-Phe-NH—$CH_2CH_2SO_3H$
33 Phe-Phe-NH—$CH_2CH_2CH_2SO_3H$
34 Phe-Phe-NH—$CH_2CH_2CH_2CH_2SO_3H$
35 Phe-Tyr-NH—$CH_2CH_2SO_3H$
36 Phe-Tyr-NH—$CH_2CH_2CH_2SO_3H$
37 Phe-Tyr-NH—$CH_2CH_2CH_2CH_2SO_3H$
38 $HO_3SCH_2CH_2$-Phe-Phe
39 $HO_3SCH_2CH_2CH_2$-Phe-Phe
40 $HO_3SCH_2CH_2CH_2CH_2$-Phe-Phe
41 $HO_3SCH_2CH_2$-Phe-Tyr
42 $HO_3SCH_2CH_2CH_2$-Phe-Tyr
43 $HO_3SCH_2CH_2CH_2CH_2$-Phe-Tyr
44 $HO_3SCH_2CH_2$-Leu-Val-Phe-Phe-Ala  (SEQ ID NO:22)
45 $HO_3SCH_2CH_2CH_2$-Leu-Val-Phe-Phe-  (SEQ ID NO:23)

-continued

| | Ala | |
|---|---|---|
| 46 | HO$_3$SCH$_2$CH$_2$CH$_2$CH$_2$-Leu-Val-Phe-Phe-Ala | (SEQ ID NO:24) |
| 47 | Leu-Val-Phe-Phe-Ala-NH—CH$_2$CH$_2$SO$_3$H | (SEQ ID NO:25) |
| 48 | Leu-Val-Phe-Phe-Ala-NH—CH$_2$CH$_2$CH$_2$SO$_3$H | (SEQ ID NO:26) |
| 49 | Leu-Val-Phe-Phe-Ala-NH—CH$_2$CH$_2$CH$_2$CH$_2$SO$_3$H | (SEQ ID NO:27) |

The compounds listed above may be modified by removing or inserting one or more amino acid residues, or by substituting one or more amino acid residues with other amino acid or non-amino acid fragments. The stereochemistry of the amino acids of the peptides above are preferably D, although they may also be of all L configuration or may be a combination of amino acids of both D and L stereochemical configuration. Retroinverso analogs of the above peptides are contemplated by the present invention. Other exemplary compounds are, e.g., detailed in copending U.S. patent application Ser. No. 09/724,842, filed Nov. 28, 2000, the text of which is incorporated herein by reference.

In another embodiment, the amyloid-targeting moiety $A_t$ is an amyloid-targeting molecule having at least one anionic group. The amyloid-targeting moiety $A_t$ may be one of Formula III:

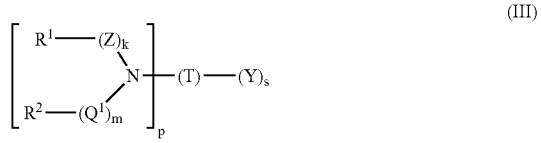

(III)

or a pharmaceutically acceptable salt or ester thereof. $R^1$ and $R^2$ are each independently a hydrogen atom or a substituted or unsubstituted aliphatic or aryl group. Z and $Q^1$ are each independently a carbonyl (C=O), thiocarbonyl (C=S), sulfonyl (SO$_2$), or sulfoxide (S=O) group. "k" and "m" are 0 or 1, provided when k is 1, $R^1$ is not a hydrogen atom, and when m is 1, $R^2$ is not a hydrogen atom. In an embodiment, at least one of k or m must equal 1. "p" and "s" are each independently positive integers selected such that the resulting compound is stable and useful as a diagnostic or therapeutic drug and the drug has an affinity for a target. T is a linking group and Y is a group of the formula -AX, wherein A is an anionic group at physiological pH, and X is a cationic group. Linking group T is, in some cases, advantageously of the formula -(CD$^1$D$^2$)$_n$-, wherein n is an integer from 1 to 25, C is carbon and D$^1$ and D$^2$ are independently hydrogen or halogen atoms; aliphatic, aromatic or heterocyclic groups; alkylamino or arylamino group; or alkyloxy or aryloxy group. In another embodiment, the amyloid-targeting moiety $A_t$ prevents, inhibits or disrupts amyloid aggregation and/or the fibrillogenic process.

In an embodiment, $R^1$ is an alkyl, alkenyl, or aryl group; k is one; Z is a carbonyl group; $R^2$ is a hydrogen atom or an alkyl group; m is zero; p and s are 1; T is an alkylene group; and $Y^1$ is SO$_3$X$^2$, where X$^2$ is H or another physiologically acceptable cation, e.g., cations of alkali metals including Li, Na, and K.

In another embodiment, $R^1$ and $R^2$ are alkyl, alkenyl, or aryl, or $R^1$ and $R^2$, taken together, form an alkylene group; k and m are each one; Z and $Q^1$ are carbonyl groups; p and s are 1; T is an alkylene group; and $Y^1$ is SO$_3$X$^2$, where X$^2$ is H or another physiologically acceptable cation.

In a further embodiment, $R^1$ is alkyl, alkenyl, or aryl; k and m are zero; $R^2$ is hydrogen or an alkyl group, p and s are each one; T is an alkylene group; and $Y^1$ is SO$_3$X$^2$, wherein X$^2$ is H$^+$ or another physiologically acceptable cation.

In another embodiment, $R^1$ and $R^2$ are alkyl, alkenyl, or aryl, or $R^1$ and $R^2$, taken together, form an alkylene group; k and m are zero; p and s are each one; T is an alkylene group; and $Y^1$ is SO$_3$X$^2$, where X$^2$ is H$^+$ or another physiologically acceptable cation.

$A_t$ may also be of Formula IIa:

(IIIa)

where $R^1$ is an alkyl, alkenyl, hydroxyalkyl, or a single-ring aromatic group; $R^2$ is a alkyl, alkenyl, hydroxyalkyl, a single-ring aromatic group, or a hydrogen atom, or $R^1$ and $R^2$, taken together with the nitrogen to which they are attached, form a heterocyclic group which is a fused ring structure; T is an alkylene group; Y is SO$_3$X, and X is a physiologically acceptable cationic group. In another embodiment, $A_t$ may be of Formula IIIa where $R^1$ is a $C_5$-$C_{18}$ alkyl, hydroxyalkyl or single-ring aromatic group; $R^2$ is a hydrogen atom or an alkyl group; T is an alkylene group; Y is SO$_3$X, and X is a cationic group. In yet another embodiment, $A_t$ may be of Formula IIa where $R^1$ and $R^2$ are alkyl, alkenyl, or single-ring aromatic groups, or $R^1$ and $R^2$, taken together with the nitrogen to which they are attached, form a heterocyclic group which is a fused ring structure; T is an alkylene group; Y is SO$_3$X, and X is a physiologically acceptable cationic group.

At may also be of Formula IIIb:

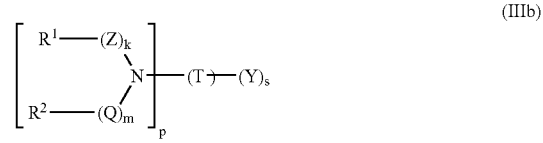

(IIIb)

where $R^1$ is an alkyl, an alkenyl, or an aromatic group; $R^2$ is a hydrogen atom, an alkyl group, or an aromatic group, or $R^1$ and $R^2$, taken together, form a heterocyclic group which is a fused ring structure; Z and Q are each independently a carbonyl (C=O), thiocarbonyl (C=S), sulfonyl (SO$_2$), or sulfoxide (S=O) group; k is 1 and m is 0 or 1; p and s are each 1; T is an alkylene group; Y is SO$_3$X, and X is a cationic group.

In another embodiment the amyloid-targeting moiety is:

(IV)

wherein Y$^-$ is an anionic group at physiological pH; $Q^b$ is a carrier molecule; X$^+$ is a cationic group; and $n^2$ is an integer selected such that the biodistribution of the targeting moiety for the intended target site is not prevented while maintaining activity of the targeting moiety.

In another embodiment, the anionic group Y is a sulfonate group. Accordingly, in this embodiment the targeting moiety is:

$$Q^b - [SO_3^- - X^+]_{n2} \quad (V)$$

In yet another embodiment, the anionic group Y is a sulfate group. Accordingly, in this embodiment the targeting moiety is:

$$Q^b - [SO_4^- - X^+]_{n2} \quad (VI)$$

The anionic group Y may also be a tetrazole group. Carrier molecules $Q^b$ may be carbohydrates, polymers, peptides, peptide derivatives, aliphatic groups, alicyclic groups, heterocyclic groups, aromatic groups and combinations thereof.

Suitable amyloid-targeting moieties $A_t$ include 3-[2-(5-amino-1,2,3,4-tetrahydro isoquinolinyl)]-1-propane sulfonic acid hydrochloride, 3[2-(5-bromo-1,2,3,4-tetrahydro isoquinolinyl)]-1-propane sulfonic acid, 2-(3-sulfopropyl)-7-amino-1,2,3,4-tetrahydroiosquinoline hydrochloride, 2-(3-sulfopropyl)-7-bromo-1,2,3,4-tetrahydroisoquinoline), Congo Red, 3-(3,4-dihydro-1H-isoquinolin-2-yl)-propane-1-sulfonic acid, (1,3,4,9-tetrahydro-b-carbolin-2-yl)-propane-1-sulfonic acid, 4-(1,3,4,9-tetrahydro-b-carbolin-2-yl)-butane-1-sulfonic acid, 2-amino-3-(3-sulfomethyl-phenyl)-propionic acid, 2-amino-3-(3-sulfomethyl-phenyl)-propionic acid, 2,5-dihydroxy-benzene-1,4-disulfonic acid, 2-(4-dimethylamino-phenyl)-3,6-dimethyl-benzothiazol-3-ium, 3-(benzothiazol-2-ylsulfanyl)-propane-1-sulfonate, 2,3-dimethyl-benzothiazol-3-ium, 3-ethyl-2-methyl-benzothiazol-3-ium, 4-[2-(4-dimethylamino-phenyl)-vinyl]-1-methyl-pyridinium, 2-[2-(4-dimethylamino-phenyl)-vinyl]-1-ethyl-pyridinium, dimethyl-(3-sulfo-propyl)-tetradecyl-ammonium.

Other suitable amyloid-targeting moieties include 2-(3-sulfo-propyl)-1,2,3,4-tetrahydro-isoquinolin-5-yl-ammonium; 5-diacetylamino-2-(3-sulfo-propyl)-isoquinolinium; 5-nitro-2-(3-sulfo-propyl)-isoquinolinium; 3-(5-bromo-3,4-dihydro-1H-isoquinolin-2-yl)-propane-1-sulfonic acid; 3-(7-nitro-3,4-dihydro-1H-isoquinolin-2-yl)-propane-1-sulfonic acid; 2-(3-sulfo-propyl)-1,2,3,4-tetrahydro-isoquinolin-7-yl-ammonium; 3-(7-bromo-3,4-dihydro-1H-isoquinolin-2-yl)-propane-1-sulfonic acid; 2-(3-Isobutoxysulfonyl-propyl)-5-methyl-1,2,3,4-tetrahydro-isoquinolinium; 3-(5-Iodo-3,4-dihydro-1H-isoquinolin-2-yl)-propane-1-sulfonic acid; 2-(3-sulfo-propyl)-9H-b-carbolin-2-ium; 2-(2-methoxycarbonyl-ethyl)-1,2,3,4-tetrahydro-isoquinolinium; 2-(3-Sulfo-propyl)-1,2,3,4-tetrahydro-isoquinolin-6-yl-ammonium; 3-(6-bromo-3,4-dihydro-1H-isoquinolin-2-yl)-propane-1-sulfonic acid; 2-(3-sulfo-propyl)-1,2,3,4-tetrahydro-isoquinoline-6-carboxylic acid methyl ester; 2-(3-sulfo-propyl)-1,2,3,4-tetrahydro-isoquinoline-5-carboxylic acid methyl ester; 2-(3-sulfo-propyl)-1,2,3,4-tetrahydro-isoquinoline-7-carboxylic acid methyl ester; 3-(6-bromo-1,3,4,9-tetrahydro-b-carbolin-2-yl)-propane-1-sulfonic acid; 3-(6-amino-1,3,4,9-tetrahydro-b-carbolin-2-yl)-propane-1-sulfonic acid; 2-(3-sulfo-propyl)-2,3,4,9-tetrahydro-1H-b-carboline-6-carboxylic acid methyl ester; 4-(6-bromo-1,3,4,9-tetrahydro-b-carbolin-2-yl)-butane-1-sulfonic acid; 4-(6-amino-1,3,4,9-tetrahydro-b-carbolin-2-yl)-butane-1-sulfonic acid; and 2-(4-sulfo-butyl)-2,3,4,9-tetrahydro-1H-b-carboline-6-carboxylic acid methyl ester.

Other suitable amyloid-targeting moieties include 3-phenylamino-1-propanesulfonic acid, 3-(4-pyridylamino)]-1-propanesulfonic acid, 3-(benzylamino)-1-propanesulfonic acid, diethylphosphonoacetic acid, phosphonoformic acid, 3-benzoylaminopropanesulfonic acid, 2-deoxy-2-(3-sulfopropyl)amino-d-glucose, 1-phenyl-2,3,-dimethyl-4-methylamino-pyrazolon-5-N-methylsulfonic acid, 3-[(−3,4-dimethyl-1-adamantyl)-amino]-1-propanesulfonic acid, 3-(2-hydroxyethyl)amino-1-propanesulfonic acid, 3-(3-hydroxy-1-propyl)amino-1-propanesulfonic acid, (−)-3-[(R)-2-hydroxy-1-propyl]amino-1-propanesulfonic acid, 3-[(d,l)-2-hydroxy-1-propyl]-1-propanesulfonic acid, 3-(4-hydroxy-1-butyl)amino-1-propanesulfonic acid, 3-(5-hydrox-1-pentyl) amino-1-propanesulfonic acid, 3-(6-hydroxy-1-hexyl) amino-1-propanesulfonic acid, 3-(4-hydroxyphenyl)amino-1-propanesulfonic acid, (+)-3-[(S)-2-hydroxy-1-propyl] amino-1-propanesulfonic acid, (+)-3-[(S)-1-hydroxy-2-propyl]amino-1-propanesulfonic acid, (−)-3-[(R)-1-hydroxy-2-propyl]amino-1-propanesulfonic acid, (+)-3-[(S)-1-hydroxy-2-butyl]amino-1-propanesulfonic acid, (−)-3-[(R)-1-hydroxy-2-butyl]amino-1-propanesulfonic acid, 3-[(dl)-5-hydroxy-2-pentyl]amino-1-propanesulfonic acid, 3-[(dl)-6-hydroxy-2-hexyl]amino-1-propanesulfonic acid, 3-amylamino-1-propanesulfonic acid, 3-hexylamino-1-propanesulfonic acid, 3-heptylamino-1-propanesulfonic acid, 3-octylamino-1-propanesulfonic acid, 3-nonylamino-1-propanesulfonic acid, 3-decylamino-1-propanesulfonic acid, 3-undecylamino-1-propanesulfonic acid, 3-dodecylamino-1-propanesulfonic acid, 3-tridecylamino-1-propanesulfonic acid, 3-tetradecylamino-1-propanesulfonic acid, 3-hexadecylamino-1-propanesulfonic acid, 3-octadecylamino-1-propanesulfonic acid, dimethyl(3-sulfopropyl)-tetradecylammonium hydroxide, inner salt, and 2-(3-sulfobutyl)-1,2,3,4-tetrahydro-9H-pyrido[3,4-b]indole.

In another embodiment, amyloid-targeting moiety $A_t$ may be 3-acetylaminopropanesulfonic acid, 3-benzoylamino-1-propanesulfonic acid, or 2-acrylamido-2-methyl-1-propanesulfonic acid.

In still other embodiments, the amyloid-targeting moiety $A_t$ may be 3-[1,2,3,4-tetrahydro-9H-pyrido(3,4-b)indolyl]-1-propanesulfonic acid, 2,5-dihydroxy-1,4-benzenedisulfonic acid, H-dLys-dLeu-dVal-dPhe-dPhe-dAla-OH (SEQ ID NO:28), Thioflavin T, Folic acid dihydrate, 3-(2-benzothiazolylthio)-1-propanesulfonic acid, 2,3-dimethylbenzothiazolium, 3-ethyl-2-methylbenzothiazolium, trans-4-[4-(dimethylamino)styryl]-1-methylpyridinium, 2-[4-(dimethylamino)styryl]-1-ethylpyridinium, or dimethyl(3-sulfopropyl)tetradecylammonium hydroxide inner salt.

In still another embodiment, amyloid-targeting moiety $A_t$ may be 3-phthalimido-1-propanesulfonic acid, N-(3-sulfopropyl)saccharin or 4-phthalimido-1-butanesulfonic acid.

In yet another embodiment, amyloid-targeting moiety $A_t$ may be 3-dimethylamino-1-propanesulfonic acid, 4-(1-piperidinyl)-1-butanesulfonic acid, 3-[1-(1,2,3,6-tetrahydropyridyl)]-1-propanesulfonic acid, 3-[2-(1,2,3,4-tetrahydroisoquinolinyl)]-1-propanesulfonic acid (preferred), 3-[2-(6,7-dimethoxy-1,2,3,4-tetrahydroisoquinolinyl)]-1-propanesulfonic acid, 3-[1-(1,2,3,4-tetrahydroquinolinyl)]-1-propanesulfonic acid, 2-(3-sulfopropyl)-1,2,3,4-tetrahydro-9H-pyrido[3,4-b]indole, 3-(1-indolinyl)-1-propanesulfonic acid(preferred), 3-[2-(6-methoxy-1,2,3,4-tetrahydroisoquinolinyl)]-1-propanesulfonic acid, 3-(2- isoindolinyl)-1-propanesulfonic acid, 3-(4-benzyl-1-piperidinyl)-1-propanesulfonic acid, 1-(3-sulfopropyl)-(S)-nicotinium hydroxide inner salt, 3-[2-(1,2,3,4,5,6,7,8-octahydroisoquinolinyl)]-1-propanesulfonic acid, Thiazol Yellow G, 3-sulfolmethylphenylalanine, Chicago Sky Blue 6B, 4-[2-(1,2,3,4-tetrahydroisoquinolinyl)]-1-butanesulfonic acid, or 3-sulfomethyl-L-phenylalanine.

Other examples of amyloid-targeting moieties include poly(vinylsulfonic acid), ethanesulfonic acid, sucrose octasulfate, 1,2-ethanediol disulfuric acid, 1,2-ethanedisulfonic acid, 1,3-propanediol disulfuric acid, 1,3-propanedisulfonic acid, 1,4-butanediol disulfuric acid, 1,4-butanedisulfonic acid, 1,5-pentanedisulfonic acid, taurine, 3-(N-morpholino) propanesulfonic acid, tetrahydrothiophene-1,1-dioxide-3,4-disulfonic acid, or 4-hydroxybutane-1-sulfonic acid, and pharmaceutically acceptable salts thereof. Other preferred amyloid-targeting moieties include 1-butanesulfonic acid, 1-decanesulfonic acid, 2-propanesulfonic acid, 3-pentanesulfonic acid, or 4-heptanesulfonic acid, and esters thereof.

In another embodiment, the amyloid-targeting moiety is 1,7-dihydroxy-4-heptanesulfonic acid, and esters thereof.

In yet another embodiment, the amyloid-targeting moiety is 2-hydroxymethyl-1,3-propanediol disulfuric acid, 2-hydroxymethyl-2-methyl-1,3-propanediol disulfuric acid, or 1,3-cyclohexanediol disulfuric acid, and esters thereof.

In still another embodiment, the amyloid-targeting moiety is 2,3,4,3',4'-sucrose pentasulfuric acid, and esters thereof.

In yet another embodiment, the amyloid-targeting moiety is 2-hydroxyethylsulfuric acid, or 3-hydroxypropylsulfamic acid sulfuric acid, and esters thereof.

In yet another embodiment, the amyloid-targeting moiety is 1,3,5,7-heptane tetrasulfuric acid or 1,3,5,7,9-nonane pentasulfuric acid, and esters thereof. In still another embodiment, the amyloid-targeting moiety $A_t$ is 3-(1H-tetrazol-5-yl)-9H-thioxanthen-9-one 10,10-dioxide, 5,5-dithiobis(1-phenyltetrazole), 1H-tetrazole, 5-phenyl-1H-tetrazole, or 5-(2-aminoethanoic acid)-1H-tetrazole; and esters thereof.

Pharmaceuticals of the invention comprising any of the above species as targeting moieties may be formulated with a variety of counter ions. Preferred counter ions may include, chloride, iodide, sodium, acetate, mixtures thereof, or other counter ions as further described herein.

The number of amino or amido groups and anionic groups in Formula III (i.e., determined by "p" and "s") are each independently selected such that the resulting compound is stable and useful as a diagnostic or therapeutic drug and the drug has an affinity for a target. Further, p and s are selected such that a sufficient number of groups, Z, $Q^1$, T and/or $Y^1$, are presented for treatment of a disease or condition. For example, the number of anionic groups is not so great as to inhibit traversal of an anatomical barrier, such as a cell membrane, or entry across a physiological barrier, such as the blood-brain barrier, in situations where such properties are desired. The integers for p and s are preferably about 1 to about 10. The values intermediate to those listed also are intended to be part of this invention, e.g., about 1 to 9, about 1 to 8, about 1 to 7, about 1 to 6, about 1 to 5, about 1 to 4, about 1 to 3, and about 1 to 2. For example, ranges of p and s using a combination of any of the above values recited as upper and/or lower limited are intended to be included. In one embodiment, p and s are integers between and including 1 and 5. In another embodiment, p and s are integers between and including 3 and 8. Linking group T is in some cases advantageously of the formula $-(CD^1D^2)_{n^1}-$, wherein $n^1$ is an integer from 1 to 25, C is carbon and $D^1$ and $D^2$ are independently a hydrogen or halogen atom; aliphatic, aromatic or heterocyclic group; alkylamino or arylamino group; or an alkyloxy or aryloxy group.

In an embodiment, still with respect to Formula III, a group of amyloid-targeting moieties include those where $R^1$ is an alkyl, alkenyl, or aryl group, k is one, Z is a carbonyl group, $R^2$ is a hydrogen atom or an alkyl group, m is zero, p and s are 1, T is an alkylene group, and $Y^1$ is $SO_3X^2$ wherein $X^2$ is $H^+$ or another physiologically acceptable cation, such as alkali metal cations. In another embodiment a group of amyloid-targeting moieties include those where $R^1$ and $R^2$ are alkyl, alkenyl, or aryl groups, or $R^1$ and $R^2$ are taken together to form an alkylene group, k and m are each one, Z and $Q^1$ are carbonyl groups, p and s are 1, T is an alkylene group, and $Y^1$ is $SO_3X^2$ where $X^2$ is $H^+$ or another physiologically acceptable cation, such as alkali metal cations.

In another embodiment a group of amyloid-targeting moieties include those where $R^1$ is an alkyl, alkenyl, or aryl group, k and m are zero, $R^2$ is hydrogen or an alkyl group, p and s are each one, T is an alkylene group, and $Y^1$ is $SO_3X^2$ wherein $X^2$ is $H^+$ or another cation, such as alkali metal cations. In another embodiment, a group of amyloid-targeting moieties include those where $R^1$ and $R^2$ are alkyl, alkenyl, or aryl groups, or $R^1$ and $R^2$ are taken together to form an alkylene group, k and m are zero, p and s are each one, T is an alkylene group, $Y^1$ is $SO_3X^2$ where $X^2$ is $H^+$ or another cation, such as alkali metal cations.

Not intending to be bound by theory, it is believed that under physiological conditions it is preferable that the nitrogen of the amyloid-targeting moiety is converted into an ammonium salt. In keeping with this theory, it is believed that acetylated nitrogens are hydrolyzed by an enzyme and converted into a positively charged ammonium group under normal physiological conditions. Likewise, in cases where the amine nitrogen is dialkylated, it is believed that the nitrogen is converted into an ammonium group by enzymatic activity. It is further believed that these conversions better enable the targeting moieties of the invention to interact with amyloid aggregates and/or amyloid precursors, e.g., cross the blood brain barrier, cross membranes, solubilize, etc., under physiological conditions in vivo.

For purposes of the present disclosure, the anionic group is negatively charged at physiological pH. Preferably, the anionic group is a sulfonate group or a functional equivalent thereof.

"Functional equivalents" of sulfonates are intended to include compounds such as sulfamates as well as bioisosteres, e.g., thiosulfates. Bioisosteres encompass both classical bioisosteric equivalents and non-classical bioisosteric equivalents. Classical and non-classical bioisosteres of sulfate and sulfonate groups are known in the art (see, e.g., Silverman, R. B., *The Organic Chemistry of Drug Design and Drug Action*, Academic Press, Inc., San Diego, Calif., pp. 19-23, 1992). Accordingly, the amyloid-targeting moiety of the invention can comprise at least one anionic group including sulfonates, sulfates, sulfamates, phosphonates, phosphates, carboxylates, and heterocyclic groups of the following formulae:

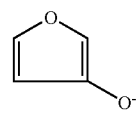

VIII

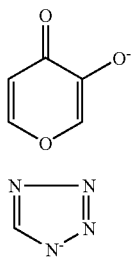

The amyloid-targeting moiety of the invention typically further comprises a counter cation (i.e., $X^1$ in Formula III). Cationic groups include positively charged atoms and moieties. If the cationic group is hydrogen, $H^+$, then the compound is considered an acid, e.g., 3-acetylamino-1-propanesulfonic acid. If hydrogen is replaced by a metal or its equivalent, the compound is a salt of the acid. Pharmaceutically acceptable salts of the targeting moiety are within the scope of the invention. For example, $X^1$ can be a pharmaceutically acceptable alkali or alkaline earth metal, polycationic counter ion or ammonium. A preferred pharmaceutically acceptable salt is a sodium salt but other salts are also contemplated within their pharmaceutically acceptable range.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs of the invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

Within the amyloid-targeting moiety of Formula III, the $Y^1$ group(s) is covalently attached to a linking group T. Linking group T is advantageously of the formula -$(CD^1D^2)_{n^1}$-, wherein $n^1$ is an integer from 1 to 25, C is carbon and $D^1$ and $D^2$ are independently a hydrogen or halogen atom; aliphatic, aromatic or heterocyclic group; alkylamino or arylamino group; or alkyloxy or aryloxy group. As such, in a preferred embodiment T is a carbohydrate, polymer, peptide or peptide derivative, aliphatic group, alicyclic group, heterocyclic group, aromatic group or combinations thereof, and may further be substituted with, e.g., one or more amino, nitro, halogen, thiol or hydroxy groups.

Another group of amyloid-targeting moieties useful in accordance with the present invention is described in U.S. Pat. No. 5,840,294.

"Linker moiety" refers to a chemical group that serves to couple the amyloid-targeting moiety to the labeling moiety while not adversely affecting either the targeting function of the amyloid-targeting moiety or the metal binding function of the labeling moiety. In certain embodiments, linker moiety $A_{lnk}$ is optional, i.e., where z=0 (and therefore a direct bond). The ability of a molecule to cross the blood-brain barrier has been shown to depend on several features inherent in the molecule, including the presence of hydrogen bonds, molecular weight and lipophilicity (see, e.g., Pardridge, W. M., *J. Neurochem.* 70, 1781-1792, (1998)). The design of such a molecule desirably should take these factors into account. To obtain optimal brain uptake of a bioconjugate molecule, a linker moiety $A_{lnk}$ should desirably incorporate: a low molecular weight, the lowest practical number of groups capable of hydrogen bonding, and $A_{lnk}$ should not significantly alter the characteristics (including lipophilicity, etc.) of $A_t$ and $A_{lab}$. Amide and hydroxy groups, among others, have been shown to reduce the ability of a molecule to cross the blood-brain barrier (see, e.g., Pardridge, W. M., cited above), whereas moieties that undergo active transport mechanisms, such as monoclonal antibodies for the insulin receptor, may increase the uptake of a molecule and are not as restrictive. Hydrocarbon linkers and chelate systems which will allow passive diffusion of targeting molecule-chelator conjugates across the blood brain barrier are contemplated to be within the present disclosure.

Suitable linker moieties include alkyl groups, which may be optionally substituted with one or more substituents and in which one or more carbon atoms may be replaced with heteroatoms such as nitrogen, oxygen, or sulfur. Other examples of $A_{lnk}$ include amino, alkylamino, arylamino, oxo, alkoxy, oxoalkyl, aryloxy, oxoaryl, thio, alkylthio, thioalkyl, arylthio, thioaryl, carbonyl, alkylcarbonyl, carbonylalkyl, arylcarbonyl, carbonylaryl, carboxyl, alkylcarboxyl, arylcarboxyl, alkyl, alkylenyl, alkeneyl, alkynyl, and aryl groups. Other suitable linker moieties include those of the formula A1-A2-A3 wherein A1 and A3 are independently N, O, or S; and A2 includes an optionally substituted alkylene group, where one or more carbon atoms may optionally be replaced with heteroatoms such as nitrogen, oxygen, or sulfur such as in poly(ethyleneglycol).

Still other suitable linker moieties include amino acids and amino acid chains functionalized with one or more reactive groups for coupling to the targeting moiety and/or labeling moiety. Preferred linker moieties include glucose and Phe.

Labeling moiety $A_{lab}$ allows the amyloid targeting imaging agents, once at the target site in vivo, to be visualized by instrumentation such as CT, MRI, ultrasound, radioisotopic or fluorescence detection. The labeling moiety either modulates an externally applied energy or generates a detectable energy itself. The labeling moiety may be an echogenic substance in the case of an ultrasound contrast agent, a paramagnetic metal chelate in the case of an MRI contrast agent, a radioactive atom (e.g., radioactive fluorine) or a chelated radioactive metal ion (e.g., In-111) in the case of a radionuclide imaging agent, a radio-opaque chelate or compound (e.g., a polyiodinated aromatic) for an x-ray contrast agent, or a fluorescent or colored dye in the case of an optical imaging contrast agent. In one embodiment labeling moiety $A_{lab}$ may be a metal chelator, e.g., as set described below. In an advantageous embodiment, $A_{lab}$ is a radionuclide (either a chelate of a metal ion or a single atom) or a paramagnetic metal ion chelate. According to one aspect of the invention, a labeled targeting molecule-chelator conjugate comprises a labeling moiety $A_{lab}$ (e.g., a radionuclide) attached directly to amyloid-targeting moiety $A_t$, therefore not requiring the use of a linker moiety.

Radiopharmaceuticals are drugs containing a radionuclide, and are used routinely in the field of radiology known as nuclear medicine for the diagnosis or therapy of various diseases. In vivo diagnostic information may be obtained by administration, e.g., by intravenous injection, of a radiopharmaceutical and determining its biodistribution using a radiation-detecting camera. The biodistribution of the radiopharmaceutical depends on the physical and chemical properties of the radiopharmaceutical and can be used to obtain information about the presence, progression, and the state of disease.

Radiopharmaceuticals can be divided into two primary classes: those whose biodistribution is determined exclusively by their chemical and physical properties and have little affinity for biological tissues; and those whose ultimate distribution is determined by their receptor binding or other biological interactions. The latter class is often called target-specific or "targeted" radiopharmaceuticals. In general, a targeted radiopharmaceuticals can be divided into: a targeting moiety, a linker moiety, and a labeling moiety which may include a metal chelator and a radionuclide or a covalently bound radioactive atom. The targeting moiety carries the radionuclide to the receptor site at the diseased tissue. The radionuclide is the detectable radiation source. The metal chelator, if present, binds strongly to the metal ion (radionuclide) via several coordination bonds, and is covalently attached to the targeting moiety either directly or through a linker moiety. Selection of a metal chelator is largely determined by the nature and oxidation state of the metallic radionuclide. The linker can be a simple hydrocarbon chain or a long poly(ethylene glycol) (PEG), which is often used for modification of pharmacokinetics. Sometimes, a metabolizable linker is used to increase the blood clearance and to reduce the background activity, thereby improving the target-to-background ratio.

The selection of a radionuclide depends on the intended medical use (diagnostic or therapeutic) of the radiopharmaceutical. The radionuclide included in $A_{lab}$ may be diagnostically as well as therapeutically useful (e.g., in the treatment of radiation-responsive diseases), a radioactive or non-radioactive metal or an oxide or nitride thereof. Examples of such radionuclides include Tc-99m, Re-186, Re-188, In-111, and Ga-67.

The coordination chemistry of the metallic radionuclide will determine the geometry of the metal chelate and the solution stability of the radiopharmaceutical. Different metallic radionuclides have different coordination chemistries, and require chelators with different donor atoms and ligand frameworks. Metal chelates which may be stored at room temperature and which do not dissociate extensively after administration are preferred.

In a particular embodiment of the invention, labeling moieties $A_{lab}$ include diagnostically or therapeutically useful radionuclides such as $^{129}I$, $^{125}I$, $^{131}I$, or $^{18}F$ for use as radiopharmaceuticals. These radionuclides, as well as their corresponding stable isotopes, may be used for diagnostic and/or therapeutic applications. These agents are typically prepared by either nucleophilic displacement of a suitable leaving group such as trifluoromethylsulfonate using, e.g., $^{18}F$, by methods known to one skilled in the art. Alternately, electrophilic substitution of a suitable group such as trialkyltin using, e.g., $Na^{129}I$ in the presence of a suitable oxidant like chloramine-T, iodogen or iodobeads, may be used, or related methods known to one skilled in the art (see, e.g., Hasrat, A. and Van Lier, J. *Synthesis*, 425, 1996). Additional methods of iodination include indirect labeling methods such as the Bolton-Hunter or stabilized Bolton-Hunter methodologies. In one embodiment the labeling moiety $A_{lab}$ includes, without limitation, Tc and Re.

According to another aspect, amyloid targeting molecule-chelator conjugates are provided where labeling moiety $A^{lab}$ is a metal chelator covalently attached to targeting moiety $A_t$ by linker moiety $A_{lnk}$. Accordingly, labeling moiety $A_{lab}$ may be a metal chelate comprising a ligand of the formula:

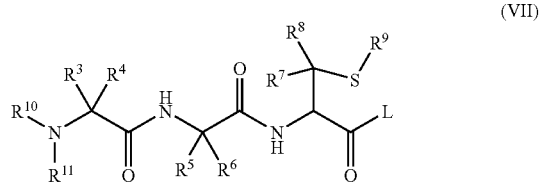

(VII)

where $R^{10}$ is a linear or branched, saturated or unsaturated $C_{1-4}$ alkylene group interrupted by one or two heteroatoms, e.g., N, O, or S. $R^{10}$ may also be optionally substituted by one or more of a halogen, hydroxyl, amino, carboxyl, $C_{1-4}$ alkyl, aryl, or C(O)R group. $R^{11}$ is H or $R^{10}$; $R^{10}$ and $R^{11}$ may, taken together, form a 5- to 8-membered saturated or unsaturated heterocyclic ring optionally substituted one or more of a halogen, hydroxyl, amino, carboxyl, oxo, $C_{1-4}$ alkyl, aryl, or C(O)R group. $R^3$, $R^4$, $R^5$ and $R^6$ may independently be a H, carboxyl, $C_{1-4}$ alkyl group (optionally substituted with, e.g., hydroxyl, amino, sulfhydryl, halogen, carboxyl, $C_{1-4}$ alkoxycarbonyl, or aminocarbonyl groups), an alpha carbon side chain of a D- or L-amino acid other than proline, and C(O)R. $R^7$ and $R^8$ may independently be a H, carboxyl, amino, $C_{1-4}$ alkyl, $C_{1-4}$ alkyl group (optionally substituted with, e.g., hydroxyl, carboxyl, amino, or C(O)R); $R^9$ may be a H or a sulfur protecting group; and L may be an hydroxyl, alkoxy, an amino acid residue, $A_t$, or $A_{lnk}$ (if present).

In an embodiment, $R^3$, $R^4$, $R^6$, $R^7$, and $R^8$ each are H; $R^5$ is $CH_2OH$; $R^9$ is acetoamidomethyl; and L is a linker moiety selected from $NH(CH_2)_3NH$ and a peptide chain consisting of one to three amino acid residues. Many chelators have been developed for this purpose. Commonly used chelating agents include DTPA (diethylenetriaminepentaacetic acid), EDTA (ethylenediaminetetraacetic acid) and DOTA (1,4,7, 10-tetraazacyclododecane-1,4,7,10-tetraacetic acid). Other chelators appropriate to link a radionuclide metal labeling moiety to a compound in accordance with the invention are described in standard texts such as Cotton, F. A. and Wilkinson, G., *Advanced Inorganic Chemistry*, 4th edition, John Wiley & Sons, 1980. However, as will be appreciated by those skilled in the art, the most suitable metal chelating agent will vary with the metal to be chelated, e.g., depending on its particular coordination.

Metal chelators suitable specifically for $^{99m}Tc$ typically present, as a metal coordinating configuration, a combination of four nitrogen and sulfur metal-coordinating atoms. Examples include chelators having $N_4$, $N_3S$, and $N_2S_2$ conformations as may be known in the art. However, such chelators may incorporate other metal-coordinating atoms including oxygen, phosphorus, and selenium. Particularly preferred for imaging applications in which it is desirable for the contrast agent to cross the blood-brain barrier after intravenous injection, e.g., in the imaging of the brain or pathologies thereof, are chelates which are lipophilic and neutral such as those described in U.S. Pat. No. 5,431,900 to Du Pont Merck Pharmaceuticals Company.

In one embodiment of the present invention, $N_2S$ chelators, such as those described in U.S. patent application Ser. Nos. 08/171,737, 08/279,155, and 08/299,636 may be used to prepare conjugates. In another embodiment, $N_2S_2$ chelators, such as those described in U.S. patent application Ser. No. 08/116,504 may also be used.

In one embodiment, a conjugate incorporates a metal chelator component that is peptidic, i.e., compatible with solid-phase synthesis. Amyloid targeting molecule-chelator conjugates of the invention may be prepared by various methods, depending on the metal chelator and/or linker moiety chosen. The peptidic metal chelator component of the labeled conjugate is conveniently prepared by techniques generally established in the art of peptide synthesis, such as the solid phase approach. Solid phase synthesis involves the stepwise addition of amino acid residues to a growing peptide chain that is linked to an insoluble support or matrix, such as polystyrene. The C-terminus residue of the peptide is first anchored to a commercially available support with its amino group protected with a N-protecting group such as t-butyloxycarbonyl group (tBoc) or a fluorenylmethoxycarbonyl (FMOC) group. The amino protecting group is removed with suitable deprotecting agents such as TFA in the case of tBoc or piperidine for FMOC and the next amino acid residue (in N-protected form) is added with a coupling agent such as dicyclocarbodiimide (DCC). Upon formation of a peptide bond, the reagents are washed from the support. After addition of the final residue, the peptide is cleaved from the support with a suitable reagent such as trifluoroacetic acid (TFA) or hydrogen fluoride (HF). The targeting moiety can be obtained commercially, and can be derivatized if necessary by techniques well known in the art. U.S. Pat. No. 5,066,789 discloses a method of conjugating peptides with chelates appropriate for use in radionuclide pharmaceuticals which may be used in conjunction with the solid-phase synthesis method outlined above.

Amyloid targeting molecule-chelator conjugates may incorporate a linker moiety that serves to couple an amyloid-targeting moiety to the metal chelator while not adversely affecting either the targeting function of the targeting moiety or the metal binding function of the chelator.

The amyloid-targeting moiety and metal chelator may be coupled to form a conjugate by reacting an appropriate functional group of the chelator or linker moiety with an appropriate functional group of the targeting moiety. For example, a free carboxyl group of a targeting moiety may be coupled to an amino group of a labeling or linker moiety.

In accordance with one aspect of the invention, amyloid targeting molecule-chelator conjugates incorporate a diagnostically useful metal capable of forming a complex. Suitable metals include radionuclides such as technetium and rhenium in their various forms such as $^{99m}TcO^{9+}$, $^{99m}TcO_2^+$, $ReO^{3+}$, and $ReO_2^+$. Incorporation of a metal within the conjugate can be achieved by various methods common in the art of coordination chemistry. When the metal is technetium-99m, the following general procedure may be used to form a technetium complex: An amyloid targeting molecule-chelator conjugate solution is formed initially by dissolving the conjugate in an alcohol such as ethanol. The solution is then degassed to remove oxygen, and then thiol protecting groups are removed with a suitable reagent such as sodium hydroxide. The solution is then neutralized with an organic acid such as acetic acid to about pH 6.0-6.5. In the labeling step sodium pertechnetate, obtained with a molybdenum generator, is added to a solution of the conjugate with an amount of a reducing agent such as stannous chloride sufficient to reduce technetium, and heated. The labeled conjugate may be separated from contaminants $^{99m}TcO_4^-$ and colloidal $^{99m}TcO_2$ chromatographically, for example with a C-18 Sep Pak™ cartridge (Alltech Assoc., Deerfield, Ill.).

In an alternate method, labeling can be accomplished by a transchelation reaction. A technetium source is a solution of technetium complexed with labile ligands facilitating ligand exchange with the selected chelator. Suitable ligands for transchelation include tartrate, citrate, and glucoheptonate. In this instance reducing agent such as stannous chloride or sodium dithionite can be used efficiently. It will be appreciated that the conjugate may be labeled using the techniques described above, or alternately the chelator itself may be labeled and subsequently coupled to the peptide to form the conjugate, a process referred to as the "preformed chelate" approach.

Another approach for labeling amyloid targeting molecule-chelator conjugates involves techniques described in U.S. patent application Ser. No. 08/152,680. Briefly, the amyloid targeting molecule-chelator conjugates are immobilized on a solid-phase support through a linkage that is cleaved upon metal chelation. This is achieved when a chelator is coupled to a functional group of the support by one of the complexing atoms. Preferably, a complexing sulfur atom is coupled to the support which is functionalized with a sulfur protecting group such as maleimide. When labeled with a diagnostically or therapeutically useful metal, amyloid targeting molecule-chelator conjugates of the invention can be used to detect or treat sites of amyloid plaque by procedures established in the art of diagnostic imaging or radiotherapy. A conjugate labeled with a radionuclide metal such as technetium-99m, rhenium-186, rhenium-188 or Y-90 may be administered to a mammal by intravenous injection in a pharmaceutically acceptable solution such as isotonic saline. The amount of labeled conjugate appropriate for administration is dependent upon the pharmacokinetic profile of the chosen conjugate in the sense that a rapidly cleared conjugate may be administered in higher doses than one that clears less rapidly. Unit doses acceptable for imaging amyloid plaques are in the range of approximately 10-20 mCi for a 70 kg individual. In vivo distribution and localization is tracked by standard scintigraphic techniques at an appropriate time subsequent to administration. The time is typically between 30 minutes and 180 minutes depending upon the rate of accumulation at the target site with respect to the rate of clearance at non-target tissue.

Yet another aspect of the present invention provides a method of treating sites of amyloid plaque, comprising administering to a subject a therapeutically effective amount of a composition comprising a targeting molecule-chelator conjugate in which the amyloid-targeting moiety $A_t$ is coupled to labeling moiety $A_{lab}$ which comprises a metal chelator complexed to a therapeutically useful metal, or an oxide or nitride thereof. One advantage to the administration of a therapeutic radionuclide is that radioactive decay and subsequent release of particulate radiation, such as an $\alpha$ or $\beta$ particle or Auger electrons, may result in the destruction of the amyloid plaque by radiolysis of the chemical bonds within the plaque. Radiation-induced damage could result in the lysis of the plaque and the formation of smaller fragments which have a more rapid biological clearance.

Magnetic resonance imaging (MRI) may be used for producing cross-sectional images of the body in a variety of scanning planes, e.g., axial, coronal, sagittal or orthogonal without exposure to radiation. MRI employs a magnetic field, radio frequency energy and magnetic field gradients to make images of the body. The contrast or signal intensity differences between tissues mainly reflect the T1 (longitudinal) and T2 (transverse) relaxation values and the proton density, which generally corresponds to the free water content, of the tissues. The T1 and T2 relaxation rates may be altered by the presence of a paramagnetic ion, for example Gd, Fe, or Cu.

MRI generally requires the use of contrast agents to assist in differentiation of the tissue of interest from the surrounding tissues in the resulting image. In the past, attention has focused primarily on paramagnetic contrast agents for MRI. Paramagnetic contrast agents involve materials which contain unpaired electrons. The unpaired electrons act as small magnets within the main magnetic field to increase the rate of longitudinal (T1) and transverse (T2) relaxation. Paramagnetic contrast agents typically comprise metal ions such as transition metal ions, which provide a source of unpaired electrons. However, since these metal ions are also generally highly toxic, the ions are typically chelated.

Contrast agents of the invention may be prepared analogously to the methods described above for the preparation of radionuclide imaging agents by substituting a paramagnetic ion source for the radionuclide source in the chelation step. Preferably, chelates of Gd have one open coordination site, and chelates of iron have no open coordination sites. Among the chelating ligands that are preferable for MRI contrast agents are EDTA, DOTA, DO3A, and DTPA. Preferred chelates of gadolinium are described in, e.g., U.S. Pat. Nos. 4,647,447, 4,957,939, and 5,362,475 to Schering AG, U.S. Pat. No. 4,899,755 to Lauffer, and U.S. Pat. Nos. 5,846,519, 4,885,363, and 5,674,470 to Bracco SpA. Convenient reagents comprising a chelating ligand, and instructions for their use in the synthesis of targeted MRI contrast agents, including solid-phase synthesis of peptidic MRI contrast agents, may be found in U.S. Pat. No. 5,637,759 to Hearst (disclosing an EDTA-containing derivatizing reagent) and in Amedio et al. Synth. Comm. 30, 3755 (2000) (disclosing a DTPA-containing derivatizing reagent). Using these reagents and the teachings of these references, one skilled in the art will appreciate how to make a contrast agent of the invention, particularly when synthesized according to a solid-phase method, e.g. a peptide targeting moiety conjugated to DTPA. Such an EDTA or DTPA ligand is typically reacted with $GdCl_3$ or $Gd_2O_3$ in buffer to make the corresponding chelate.

Alternatively, MRI contrast agents may comprise a superparamagnetic iron oxide particle, e.g., as described in U.S. Pat. No. 5,219,554 entitled, "Biodegradable super-paramagnetic materials—used as contrast agents for in vivo magnetic resonance imaging of organs or tissue", or U.S. Pat. No. 6,123,920 to Nycomed Imaging AS.

Ultrasound is another valuable diagnostic imaging technique and provides certain advantages over other diagnostic techniques. Ultrasound involves the exposure of a patient to sound waves. Generally, the sound waves dissipate due to absorption by body tissue, penetrate through the tissue or reflect off of the tissue. The reflection of sound waves off of tissue, generally referred to as backscatter or reflectivity, forms the basis for developing an ultrasound image. In this connection, sound waves reflect differentially from different body tissues. This differential reflection is due to various factors, including the constituents and the density of the particular tissue being observed. Ultrasound involves the detection of the differentially reflected waves, generally with a transducer that can detect sound waves having a frequency of one megahertz (mHz) to ten mHz. The detected waves can be integrated into an image which is quantitated and the quantitated waves converted into an image of the tissue being studied. Ultrasound also generally involves the use of contrast agents such as suspensions of solid particles, emulsified liquid droplets, and gas-filled bubbles or vesicles.

Ultrasound contrast agents typically comprise an echogenic substance, typically a gas or a liquid which is easily vaporized upon ultrasound exposure. The echogenic substance may be encapsulated in lipids, as described in U.S. Pat. Nos. 6,146,657, 5,088,499, 6,139,819, 6,033,645, 6,071,495, and 5,088,499 to Unger. Other substances, for example polymers and denatured albumin, may also be used as the encapsulating substance as described in U.S. Pat. Nos. 6,083,484, 5,976,501, 5,820,850 to Molecular Biosystems. The selection of echogenic substance, particularly fluorinated alkanes, is discussed in U.S. Pat. Nos. 5,573,751 and 5,558,854 to Quay. U.S. Pat. Nos. 5,795,562, 5,676,925, and 5,928,626 to Nycomed Imaging AS disclose further examples of ultrasound-detectable vesicles. Also discussed in these references are a variety of methods of derivatizing ultrasound vesicles to covalently bind targeting groups.

The imaging agents of the present invention may be adapted for use in the aforementioned imaging and diagnostic techniques for the imaging of amyloid-related conditions in vivo. This may be done by using the linking moiety $A_{lnk}$ to "bridge" the targeting moiety to the labeling moiety, and including the appropriate labeling moiety for the intended imaging use, e.g., ultrasound, CT, etc. The targeting moiety may be incorporated in a variety of ways. Generally speaking, the targeting moiety may be incorporated by being associated covalently or non-covalently with the labeling moiety. In the case of a metal chelator (for radiolabeling), this is done generally by covalently bonding the targeting moiety to the chelator moiety, e.g., through the use of a linker moiety. In the case of e.g., ultrasound imaging agents which utilize, e.g., lipid vesicles, the targeting moiety $A_t$ may be covalently or non-covalently associated with or one or more of the materials which are included in the vesicles, including lipids, proteins, polymers and/or auxiliary stabilizing materials.

Exemplary covalent bonds by which the targeting moiety is associated with vesicles include amide (—CONH—); thioamide (—CSNH—); ether (ROR', where R and R' may be the same or different and are other than hydrogen); ester (—COO—); thioester (—COS—); —O—; —S—; —$S_n$—, where n is greater than 1, preferably about 2 to about 8; carbamates; —NH—; —NR—, where R is alkyl; urethane; and substituted inidate; and combinations of two or more of these. Covalent bonds between targeting moieties and, e.g., lipids, may be achieved through the use of molecules that may act as spacers to increase the conformational and topographical flexibility of the moiety. Examples of such spacers include succinic acid, 1,6-hexanedioic acid, 1,8-octanedioic acid, and the like, as well as modified amino acids, such as 6-aminohexanoic acid, 4-aminobutanoic acid. In addition, in the case of targeting ligands which comprise peptide moieties, sidechain-to-sidechain crosslinking may be complemented with sidechain-to-end crosslinking and/or end-to-end crosslinking. Also, small spacer molecules such as dimethylsuberimidate may be used to accomplish similar objectives. The use of agents, including those used in Schiff's base-type reactions, such as gluteraldehyde, may also be employed. The Schiff's base linkages, which may be reversible linkages, can be rendered more permanent covalent linkages via the use of reductive amination procedures.

This may involve, for example, chemical reducing agents, such as lithium aluminum hydride reducing agents or their milder analogs, including lithium aluminum diisobutyl hydride (DIBAL), sodium borohydride (NaBH$_4$) or sodium cyanoborohydride (NaBH$_3$CN).

As discussed above, compositions of the invention including gas and/or gaseous precursor filled vesicles, are useful as contrast agents for diagnostic imaging, including, for example, ultrasound imaging (US), computed tomography (CT) imaging, including CT angiography (CTA) imaging, magnetic resonance (MR) imaging, including magnetic resonance angiography (MRA), nuclear medicine, optical imaging and elastography.

In accordance with the present invention, there are provided methods of imaging one or more regions of a patient. The methods of the invention involve the administration of an imaging agent of the invention, e.g., as a contrast medium, in the form of a lipid and/or vesicle composition, to a patient. The patient is scanned using diagnostic imaging including, e.g., ultrasound, to obtain visible images of an internal region of a patient.

Administration of the lipid and/or vesicle compositions of the invention can be carried out in various fashions, e.g., parenterally, orally, or intraperitoneally. Parenteral administration includes administration by the following routes: intravenous; intramuscular; interstitially; intra-arterially; subcutaneous; intraocular; intrasynovial; transepithelial, including transdermal; pulmonary via inhalation; ophthalmic; sublingual and buccal; topically, including ophthalmic; dermal; ocular; rectal; and nasal inhalation via insufflation. Intravenous administration is preferred among the routes of parenteral administration. The useful dosage to be administered and the particular mode of administration will vary depending upon the age, weight and the particular mammal and region thereof to be scanned, and the particular imaging agent employed. Various combinations of the lipid compositions may be used to alter properties as desired, including viscosity, osmolarity or palatability. In carrying out the imaging methods of the present invention, the imaging agent can be used alone, or in combination with diagnostic, therapeutic or other agents.

In the case of diagnostic applications, such as ultrasound and CT, energy, such as ultrasonic energy, is applied to at least a portion of the patient to image the target tissue. A visible image of an internal region of the patient is then obtained, such that the presence or absence of diseased tissue can be ascertained.

In addition to the pulsed method, continuous wave ultrasound such as Power Doppler may be applied. This may be particularly useful where rigid vesicles, for example, vesicles formulated from polymethyl methacrylate, are employed. In this case, the relatively higher energy of the Power Doppler may be made to resonate the vesicles and thereby promote their rupture. This can create acoustic emissions which may be in the subharmonic or ultraharmonic range or, in some cases, in the same frequency as the applied ultrasound. In addition, the process of vesicle rupture may be employed to transfer kinetic energy to the surface, for example of a plaque, to promote amyloid plaque lysis. Thus, therapeutic plaque lysis may be achieved during a combination of diagnostic and therapeutic ultrasound. Spectral Doppler may also be employed. The levels of energy from diagnostic ultrasound may be insufficient to promote the rupture of vesicles and to facilitate release and cellular uptake of the bioactive agents. As noted above, diagnostic ultrasound may involve the application of one or more pulses of sound. Pauses between pulses permit the reflected sonic signals to be received and analyzed. The limited number of pulses used in diagnostic ultrasound limits the effective energy which is delivered to the tissue that is being studied.

Higher energy ultrasound, for example, ultrasound which is generated by therapeutic ultrasound equipment, is generally capable of causing rupture of the vesicle species. In general, devices for therapeutic ultrasound employ from about 10 to about 100% duty cycles, depending on the area to be treated with the ultrasound. Areas of the body which are generally characterized by larger amounts of muscle mass, for example, backs and thighs, as well as highly vascularized tissues, such as heart tissue, may require a larger duty cycle, for example, up to about 100%.

In connection with methods involving ultrasonic imaging, particularly in embodiments involving vesicles, diagnostic ultrasound imaging may be carried out simultaneously with the application of therapeutic ultrasonic waves so as to rupture the vesicles for purposes such as enhanced cavitation or the targeted release of a bioactive agent combined with the vesicles. The method comprises the steps of (i) administering to the patient a quantity of vesicles; (ii) insonating the vesicles in a region of the patient with therapeutic ultrasonic waves at a frequency and energy to cause the vesicles to rupture; and (iii) simultaneously receiving ultrasonic emissions from the insonated vesicles at a harmonic of the frequency of the therapeutic ultrasonic waves and generating an image of said region from the received ultrasonic emissions. Simultaneous imaging allows an operator to monitor the rupture of the vesicles in real time.

An aspect of the invention provides a method of imaging amyloid plaques, comprising administration of a diagnostically effective amount of a composition having an amyloid targeting molecule-chelator conjugate where the amyloid-targeting moiety $A_t$ is coupled to a labeling moiety $A_{lab}$ having a metal chelator complexed to a diagnostically useful metal, or an oxide or nitride thereof; and which binds to amyloid plaques.

Amyloid targeting molecule-chelator conjugates, when complexed with a diagnostically useful metal, are useful for imaging sites of amyloid plaque. The invention also provides targeting molecule-chelator conjugates that, when complexed with a therapeutically useful metal, are useful for treating sites of amyloid plaque. An amyloid targeting molecule-chelator conjugate incorporates an amyloid-targeting moiety coupled to a linker moiety or a labeling moiety comprising a metal chelator. In an embodiment of the present invention, the targeting moiety is coupled to the metal chelator, e.g., as in Formula VII above. Metal chelators for use in the invention include those disclosed in PCT publication WO 96/03427, published Feb. 8, 1996.

Diagnostic kits provided by the invention include amyloid targeting imaging agents as described herein; a reducing agent; a buffering agent; a transchelating agent, and instructions for use of the kit. The kit provides all the components required to prepare, e.g., a detectable labeled conjugate for diagnostic use, with the exception of the detectable label which is desirably generated at the clinical site. The components of the kit can be provided in powder form that is readily prepared into an injectable solution on reconstitution with an aqueous solvent. This solution can then be admixed with an appropriate amount of detectable label, e.g., radionuclide metal appropriate for the imaging technique to be employed, and immediately used to image a target site.

In one embodiment, the amyloid-targeting moiety disclosed herein prevents or inhibits amyloid protein assembly into insoluble fibrils which, in vivo, are deposited in various organs. It is also believed, without limitation, that the amyloid-targeting moiety also prevents the amyloid protein, whether in soluble or non-soluble form, from binding or adhering to a cell surface and causing cell damage or toxicity.

Equivalents

Those skilled in the art will recognize, or be able to ascertain using no more than routine experimentation, numerous equivalents to the specific procedures described herein. Such equivalents are considered to be within the scope of this invention and are covered by the following claims. The contents of all references, issued patents, and published patent applications cited throughout this application are hereby incorporated by reference.

What is claimed is:

1. An amyloid-targeting imaging agent of the formula $$A_t \text{---} (A_{lnk})_z \text{---} A_{lab} \quad (I)$$

where z is 0 or 1; $A_t$ is an amyloid targeting moiety selected from the group consisting of NaO$_3$SCH$_2$(CH$_2$)$_4$CH$_2$SO$_3$Na,
NaO$_3$SNHCH$_2$CH$_2$CH$_2$OSO$_3$Na,

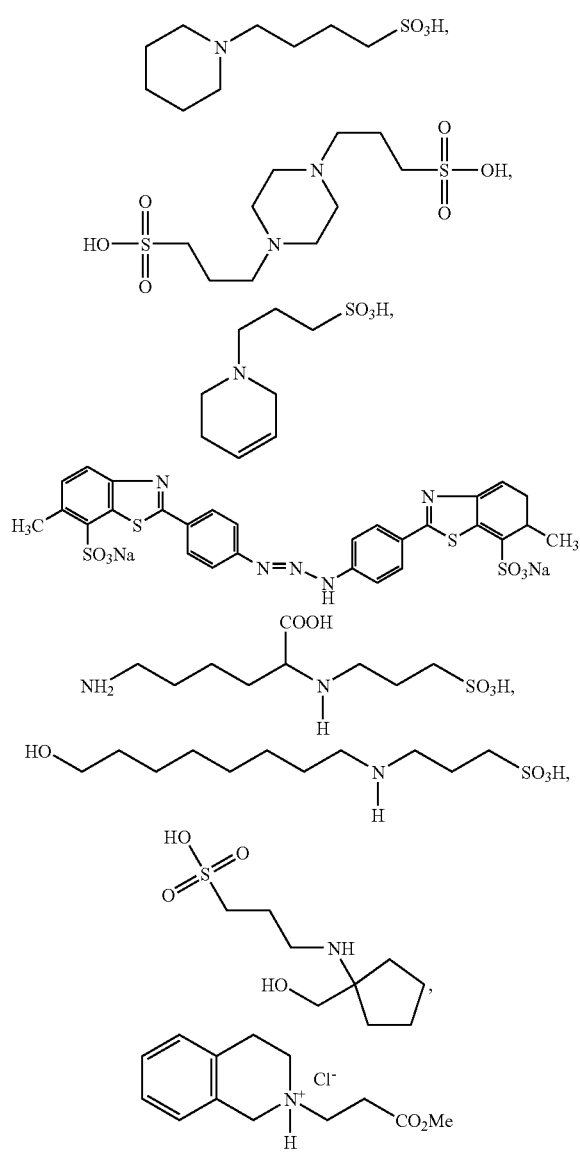

and pharmaceutically acceptable salts thereof;
$A_{lnk}$ is a linker moiety; and $A_{lab}$ is a labeling moiety.

2. The amyloid-targeting imaging agent of claim 1, wherein $A_{lab}$ includes a radionuclide selected from $^{99m}$Tc, $^{99}$Tc, $^{64}$Cu, $^{67}$Cu, $^{97}$Ru, $^{109}$Pd, $^{186}$Re, $^{188}$Re $^{111}$In, $^{113m}$In, $^{153}$Gd, $^{90}$Y, $^{153}$Sm, $^{166}$Ho, $^{198}$Au, $^{199}$Au, $^{90}$Sr, $^{89}$Sr, $^{105}$Rh, $^{201}$Tl, $^{51}$Cr, $^{67}$Ga, $^{57}$co, $^{60}$Co, $^{123}$I, $^{125}$I, $^{131}$I or $^{18}$F.

3. The amyloid-targeting imaging agent of claim 1, wherein $A_{lab}$ includes a radionuclide selected from the group consisting of Tc and Re.

4. The amyloid-targeting imaging agent of claim 1, wherein $A_{lab}$ is a metal chelate of a radioactive or paramagnetic metal ion.

5. The amyloid-targeting imaging agent of claim 1, wherein $A_{lab}$ comprises a chelating ligand of the formula

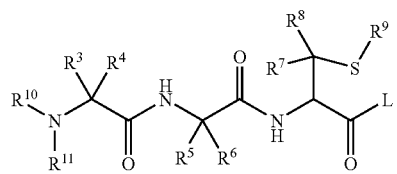

where $R^{10}$ is a linear or branched, saturated or unsaturated $C_{1-4}$ alkylene group interrupted by one or two heteroatoms; $R^{11}$ is H or $R^{10}$, or $R^{10}$ and $R^{11}$ taken together, form a 5- to 8-membered saturated or unsaturated heterocyclic ring optionally substituted with one or more of halogen, hydroxyl, amino, carboxyl, oxo, $C_{1-4}$ alkyl, aryl, or C(O)R groups; $R^3$, $R^4$, $R^5$ and $R^6$ are independently H, carboxyl, $C_{1-4}$ alkyl, an alpha carbon side chain of a D- or L-amino acid other than proline, or C(O)R; $R^7$ and $R^8$ are independently H, carboxyl, amino, $C_{1-4}$ alkyl, $C_{1-4}$ alkyl; $R^9$ is H or a sulfur protecting group; and L is hydroxyl, alkoxy, an amino acid residue, or a linking group.

6. A kit for preparing a radiopharmaceutical preparation, said kit comprising:
an amyloid-targeting imaging agent of claim 1;
a reducing agent;
a buffering agent;
a transchelating agent, and
instructions for the preparation and use of the radiopharmaceutical in the imaging of amyloid or an amyloid-related condition.

7. A method of diagnostic medical imaging of an amyloid-associated disease comprising the steps of administering to a patient a pharmaceutical composition according to claim 1 and then imaging said patient.

8. The method of diagnostic medical imaging according to claim 7 wherein $A_{lab}$ of said pharmaceutical composition is a radiopharmaceutical.

9. The method of diagnostic medical imaging according to claim 7 wherein $A_{lab}$ of said pharmaceutical composition is a metal chelate.

10. The method of diagnostic medical imaging according to claim 9 wherein said metal chelate is gadolinium-DTPA, gadolinium-DOTA, or gadolinium-DO3A.

11. The method of diagnostic medical imaging according to claim 9 wherein said metal chelate is a chelate of $^{99m}$Tc or $^{111}$In.

12. The method of diagnostic medical imaging according to claim 7 wherein said imaging step is ultrasound imaging.

13. A method for imaging amyloid deposition in a patient, comprising administering an amyloid-targeting imaging agent according to claim 1 to a patient, and imaging said amyloid-targeting imaging agent in said patient to determine the presence of amyloid in said patient.

14. The method of claim 13, wherein said imaging step is radionuclide imaging.

15. The method of claim 14, wherein said imaging step is SPECT imaging.

16. The method of claim 13, wherein said imaging step is magnetic resonance imaging.

17. The method of claim 13, wherein said imaging step is ultrasound imaging.

18. The method of claim 13, wherein said imaging step is X-ray imaging.

19. The method of claim 13, wherein said imaging step is fluorescence imaging.

20. A method for diagnostic medical imaging of an amyloid-associated disease in a patient, comprising administering to a patient a pharmaceutical composition comprising an amyloid-targeting imaging agent of claim 1, and imaging the amyloid-targeting imaging agent in said patient.

21. The method of claim 20, wherein $A_{lab}$ of said pharmaceutical composition is a radiopharmaceutical.

22. The method of claim 20, wherein $A_{lab}$ of said pharmaceutical composition is a metal chelate.

23. The method of claim 20, wherein $A_{lab}$ of said pharmaceutical composition is a metal chelate and said imaging step is magnetic resonance imaging or radionuclide imaging.

24. The method of claim 22, wherein said metal chelate is gadolinium DTPA, gadolinium-DOTA, or gadolinium-DO3A.

25. The method of claim 22, wherein said metal chelate is a chelate of $^{99m}$Tc or $^{111}$In.

26. The method of claim 20, wherein said imaging step is ultrasound imaging.

27. A method for diagnosing an amyloid-related condition in a patient, comprising administering an amyloid-targeting imaging agent according to claim 1 to a patient, and imaging said amyloid-targeting imaging agent in said patient to determine the presence of amyloid in said patient, such that the presence or absence of an amyloid-related condition in sad patient is determined.

28. The method of claim 27, wherein said amyloid-related condition is selected from the group consisting of Creutzfeld-Jakob Disease (CJD), Kuru, transmissible cerebral amyloidosis, transmissible virus dementias, familial CJD, scrapie, transmissible mink encephalopathy, bovine spongiform encephalopathy (BSE), inflammation-associated amyloid, type II diabetes, primary amyloidosis, feline spongiform encephalopathy, non-transmissible cerebral amyloidosis, prion-mediated diseases, dialysis-related amyloidosis, light chain-related amyloidosis, cerebral amyloid angiopathy, and Alzheimer's disease.

29. The amyloid-targeting imaging agent of claim 1, wherein the amyloid targeting moiety is of the formula

or a pharmaceutically acceptable salt thereof.

30. The amyloid-targeting imaging agent of claim 1, wherein the amyloid targeting moiety is of the formula

or a pharmaceutically acceptable salt thereof.

31. The amyloid-targeting imaging agent of claim 1, wherein the amyloid targeting moiety is of the formula

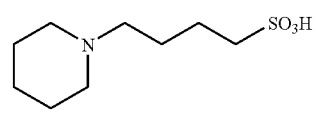

or a pharmaceutically acceptable salt thereof.

32. The amyloid-targeting imaging agent of claim 1, wherein the amyloid targeting moiety is of the formula

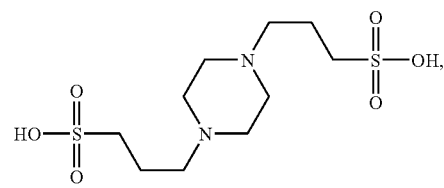

or a pharmaceutically acceptable salt thereof.

33. The amyloid-targeting imaging agent of claim 1, wherein the amyloid targeting moiety is of the formula

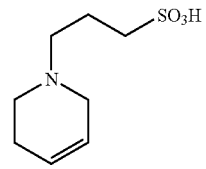

or a pharmaceutically acceptable salt thereof.

34. The amyloid-targeting imaging agent of claim 1, wherein the amyloid targeting moiety is of the formula

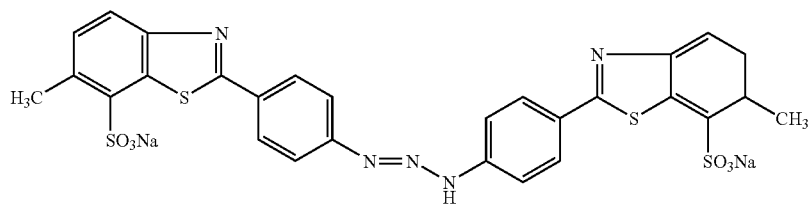

or a pharmaceutically acceptable salt thereof.

35. The amyloid-targeting imaging agent of claim 1, wherein the amyloid targeting moiety is of the formula

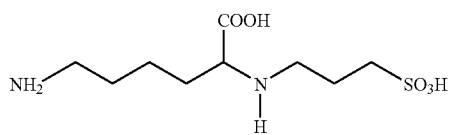

or a pharmaceutically acceptable salt thereof.

36. The amyloid-targeting imaging agent of claim 1, wherein the amyloid targeting moiety is of the formula

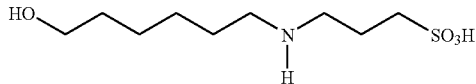

or a pharmaceutically acceptable salt thereof.

37. The amyloid-targeting imaging agent of claim 1, wherein the amyloid targeting moiety is of the formula

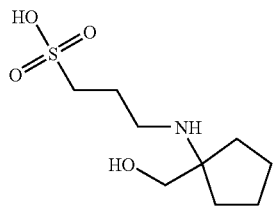

or a pharmaceutically acceptable salt thereof.

38. The amyloid-targeting imaging agent of claim 1, wherein the amyloid targeting moiety is of the formula

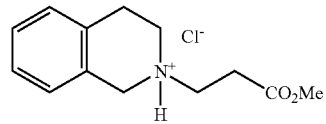

or a pharmaceutically acceptable salt thereof.

* * * * *